US006985762B2

(12) United States Patent
Brashears et al.

(10) Patent No.: US 6,985,762 B2
(45) Date of Patent: *Jan. 10, 2006

(54) NETWORK FORMATTING FOR REMOTE LOCATION OXIMETRY APPLICATIONS

(75) Inventors: Michael K. Brashears, Denver, CO (US); Tricia Dessel, Boulder, CO (US); James Galbiati, Boulder, CO (US); Charles Gonzales, Westminster, CO (US); David L. Newcomb, Louisville, CO (US); Gilbert Van Hoy, Broomfield, CO (US)

(73) Assignee: Datex-Ohmeda, Inc., Madison, WI (US)

( * ) Notice: Subject to any disclaimer, the term of this patent is extended or adjusted under 35 U.S.C. 154(b) by 154 days.

This patent is subject to a terminal disclaimer.

(21) Appl. No.: 10/190,888

(22) Filed: Jul. 2, 2002
(Under 37 CFR 1.47)

(65) Prior Publication Data

US 2004/0102687 A1  May 27, 2004

Related U.S. Application Data

(63) Continuation-in-part of application No. 09/386,691, filed on Aug. 30, 1999, now Pat. No. 6,415,166, which is a continuation-in-part of application No. 08/938,224, filed on Sep. 26, 1997, now abandoned.

(51) Int. Cl.
  *A61B 5/00* (2006.01)
(52) U.S. Cl. .................. 600/323; 600/333; 128/904
(58) Field of Classification Search ............... 600/300, 600/301, 310, 322, 323, 324, 333; 128/903, 128/904; 358/400, 403, 434; 715/522
See application file for complete search history.

(56) References Cited

U.S. PATENT DOCUMENTS

| | | | | |
|---|---|---|---|---|
| 5,078,136 A | * | 1/1992 | Stone et al. | 600/310 |
| 5,161,222 A | * | 11/1992 | Montejo et al. | 719/321 |
| 5,348,004 A | * | 9/1994 | Hollub | 600/323 |
| 5,515,176 A | * | 5/1996 | Galen et al. | 358/403 |
| 5,544,649 A | * | 8/1996 | David et al. | 128/904 |
| 5,579,378 A | * | 11/1996 | Arlinghaus, Jr. | 128/904 |
| 5,581,369 A | * | 12/1996 | Righter et al. | 128/904 |
| 5,701,894 A | * | 12/1997 | Cherry et al. | 600/300 |
| 6,260,021 B1 | * | 7/2001 | Wong et al. | 705/2 |
| 6,409,660 B1 | * | 6/2002 | Sjoqvist | 600/300 |

* cited by examiner

*Primary Examiner*—Eric F. Winakur

(74) *Attorney, Agent, or Firm*—Marsh Fischmann & Breyfogle LLP

(57) ABSTRACT

The present invention provides an apparatus and method for formatting data from a pulse oximetry monitoring device to include display layout information for use by a remotely located display unit. In this regard, the remotely located display unit is in data communication with the pulse oximetry through a communications network. The data communications network may be an analog network such as a telephony network or a digital network such as the internet. In any case, upon receiving the pulse oximetry data, a remote display device may utilize the display layout information to provide an output of the monitored data. This output may be a visual display or a hard copy output.

15 Claims, 29 Drawing Sheets

Section 1:     Monitor information
                    Type of medical monitor
                    Version #
                    Serial #
                    Data collection software program name
                    Software version #

Section 2:  Parameter definitions
                    Each parameter definition contains:
                        Parameter id
                        Parameter name
                        Data type (integer, floating point, character text,
                                boolean, time stamp, graphical picture, etc)
                        Data size (number of bytes one data point takes up)
                        Expected frequency of transmission
                        Max and minimum possible values Section 3:     Default parameter display settings -
               Each display setting contains:
                    Parameter id - the parameter being set-up.
                    Parameter label
                    Screen location of label
                    Text size of label
                    Foreground and background text color of label
                    Display Current Value, or display graphical trace over time.
                    For Current Value
                        Screen location of current value
                        Text size of current value
                        Foreground and background text color of current value
                    For graphical trace
                        Amount of time to display.
                        Auto-scale, or fixed Y axis scale.
                        Trace color
                        Point style (not displayed, X, circle, plus sign, dot, etc)
                    Allow user to modify display settings (True/False)

Section 4:     Patient data
                    Patient name
                    Encrypted password
                    Physician name
                    Hospital or facility name
                    Time stamp of start of data Section 5:     Data packets
               Each data packet contains
                    Timestamp
                    Parameter id
                    Parameter data

Fig. 5

| Byte Stream Data | Description |
|---|---|
| | Section 1 |
| 0 | Monitor information follows |
| "3900 Pulse Oximeter" | Name of monitor |
| 0 | End of monitor name |
| | Version # not available for this monitor type |
| 0 | End of version # |
| | Serial # not available for this monitor type |
| 0 | End of serial # |
| "3900 Data Collection" | Data collection software program name |
| 0 | End of software program name |
| "1.0" | Software version # |
| | Section 2 |
| 1 | First Parameter Definition follows |
| 0 0 | Parameter id is 0 (2 bytes) |
| "SpO2" | Parameter name |
| 1 | Data type is IEEE floating point |
| 4 | 32 bit data size (4 bytes) |
| 0 0 0 30 | Expected frequency - 4 bytes (30 samples/min) |
| 0 0 200 66 | Max value - 4 bytes (100.0 in IEEE floating point) |
| 0 0 0 0 | Min value (0.0 in IEEE floating point) |
| 1 | Parameter Definitions 2- N follow |
| | Section 3 |
| 1 | Parameter default setting follows |
| 0 0 | First Parameter 0 is being set-up (2 bytes) |
| "SpO2" | Parameter label |
| 0 | end of parameter label |
| 10 | X coordinate of label screen location, on scale 0 to 255 |
| 80 | Y coordinate of label screen location, on scale 0 to 255 |
| 10 | Text size of label |
| 255 255 255 | Label foreground color (3 bytes, RGB values, this is WHITE) |
| 0 0 0 | Label background color (3 bytes, RGB values, this is BLACK) |
| 0 | Display Current Value |
| 150 | X coordinate of current value |
| 80 | Y coordinate of current value |
| 18 | Text size of label |
| 255 255 255 | Label foreground color (this is WHITE) |
| 0 0 0 | Label background color (this is BLACK) |
| 1 | Allow user to modify display settings |
| 1 | Parameter default settings 2-N follow |

Fig 7a

| | |
|---|---|
| | Section 4 |
| "John Doe" | Patient name |
| 0 | end of Patient name |
| "*&HH)839*(#)+;-8shA" | Encrypted password |
| 0 | end of Encrypted password |
| | Physician name not supplied |
| 0 | end of Physician name |
| | Hospital or facility name not supplied |
| 0 | end of Hospital or facility name |
| 60 146 133 247 | Time stamp - seconds since 1-1-70 - 4 bytes |
| 0  174 | Time stamp - milliseconds - 2 bytes |
| 7 | Time stamp - time zone |
| | Section 5 |
| 2 | Data packet follows |
| 0  0 | Seconds since start of file (2 bytes) |
| 0  0 | milliseconds in current second (2 bytes) |
| 0 | Parameter 0  (ie SpO2) |
| 0 0 189 0 | value of 94.5, in IEEE 32 bit floating point format |
| 2 | Data packet follow for Parameters 2-N |
| *** | Additional data packet sets would follow |

Fig. 7b

PULSE OXIMETRY INSTAREPORT

601 — H GONZALES
110
DR CASEY
GENERAL

602 — BY
COMMENTS

STUDY DURATION AND VALUES

603 — STUDY START DATE/TIME: 01/02/99 00:00:00
604 — STUDY END DATE/TIME: 01/03/99 12:00:00

| | | PR | TIME |
|---|---|---|---|
| LOW SpO2 | 81% | 134 BPM | 00:58:05 |
| AVERAGE SpO2 | 91% | | |
| SpO2 STD. DEV. | 8% | | |

605 — STUDY DURATION: 12:00:00   606

| | | SpO2 | TIME |
|---|---|---|---|
| HIGH PR | 100 BPM | 90% | 02:00:00 |
| LOW PR | 61 BPM | 80% | 04:58:06 |
| AVERAGE PR | 72 BPM | | |

607 — # SpO2 VALUES BELOW 85%: 130
608 — TOTAL DURATION BELOW 85%: 00:13:34

609 — TOTAL TIME

| SpO2 range | % |
|---|---|
| 0-70% | 0 |
| 71-75% | 0 |
| 76-80% | 0 |
| 81-85% | 7% |
| 86-90% | 12% |
| 91-95% | 20% |
| 96-100% | 61% |

PULSE OXIMETRY INSTAREPORT                              PAGE 1 OF 2

FIG. 14A

701 — H GONZALES
110
DR CASEY
GENERAL

702 — BY: _____
COMMENTS: _____
_____
_____

703 — STUDY DATE:
05/16/98

704 — ALARM LEGEND
HIGH SpO$_2$ ............................ ↕ — 716
LOW SpO$_2$ ............................ ↕ — 717
NO SENSOR ............................ ! — 718
SENSOR OFF ............................ ? — 719

705 — 6-SECOND FORMAT
SpO$_2$

706 — TIME   ▽  50 60 70 80 90 100  SpO$_2$

707 —
12:34  80   |  |  |  |  |  |    95
12:34  82   |  |  |  |  |  |    95
12:34  84   |  |  |  ┌─┤  |    80↓
12:35  86   |  |  |  │ │  |    80↓
12:35  88   |  |  |  └─┘  |    95
12:35  90   |  |  |  |  |  |    95

STUDY DURATION AND VALUES
START DATE/TIME:
708 — 05/16/98   12:34

709 — END DATE/TIME:
05/16/98   12:35

710 — STUDY DURATION:
00:01:00

TIME
711 —
LOW SpO$_2$         80%      84 ▽   12:35
HIGH PR                      90 ▽
LOW PR                       80 ▽
AVERAGE SpO$_2$              90%
SpO$_2$ STD.DEV              ———

SUMMARY STATISTICS
%TIME PER SpO$_2$ RANGE
       0  20  40  60  80  100  %
712 —
90-100  ████████████        67
85-89                        0
80-84   ██████              33
70-79                        0
0-69                         0

TIME PER SpO$_2$ RANGE
713 —
    90-100%       00:00:24
    85-89%        00:00:00
    80-84%        00:00:12
    70-79%        00:00:00
    0-69%         00:00:00

714 — # SpO2 VALUES BELOW 85%:
2

715 — TOTAL DURATION BELOW 85%:
00:00:12

FIG. 15

801 — TREND DATA OUTPUT
6 SECONDS PER DATA POINT

802 — P HERNANDEZ
93256
JP CLAIR
GENERAL

803 — 09/03/98

804 —
| | | | | |
|---|---|---|---|---|
| 14:01:31 | SpO2= 80 | PR= 70 | PI=1.38 | ·· LOW SpO2 |
| 14:01:25 | SpO2= 81 | PR= 70 | PI=1.43 | ·· LOW SpO2 |
| 14:01:19 | SpO2= 81 | PR= 70 | PI=1.48 | ·· LOW SpO2 |
| 14:01:13 | SpO2= 97 | PR= 70 | PI=1.56 | |
| 14:01:07 | SpO2= 99 | PR= 70 | PI=2.14 | |
| 14:01:01 | SpO2=100 | PR= 70 | PI=0.47 | |
| 14:00:55 | SpO2=100 | PR= 69 | PI=...... | |
| 14:00:49 | SpO2=..... | PR=.... | PI=...... | ·· NO SENSOR |
| 14:00:43 | SpO2=..... | PR=.... | PI=...... | ·· NO SENSOR |
| 14:00:37 | SpO2=..... | PR=.... | PI=...... | ·· NO SENSOR |

END TREND DATA

FIG. 16

NETWORK FORMATTING FOR REMOTE LOCATION OXIMETRY APPLICATIONS

CROSS-REFERENCE TO RELATED APPLICATIONS

This application is a continuation-in-part of U.S. patent application Ser. No. 09/386,691 entitled "Photoplethysmographic Device With Remote Facsimile," filed on Aug. 30, 1999, now U.S. Pat. No. 6,415,166, which is a continuation-in-part of U.S. patent application Ser. No. 08/938,224, entitled "Photoplethysmographic Device With Remote Facsimile," which was filed on Sep. 26, 1997, now abandoned. The disclosure of both of those applications is incorporated herein by reference in its entirety herein.

FIELD OF THE INVENTION

The present invention relates generally to the field of remote medical monitoring systems. In particular, the present invention provides a system and method for processing data collected from a medical monitoring device for transfer over a network, such as the Internet, where that data may be output by a remotely located output device.

BACKGROUND

In a variety of contexts, it is desirable to remotely monitor a patient via a data or other network. In particular, with the recent expansion of data communication networks, such as the Internet and the associated World Wide Web, remote patient monitoring has become an increasingly viable health care option. In this regard, a medical monitoring device may be interconnected to data communications networks, such as the Internet, to transmit patient data to a remote user who is also interconnected to that data communications network. These remote patient monitoring systems allow, inter alia, physician access to geographically remote patients as well as at home monitoring for non-critical patients.

Generally, existing medical monitoring devices that provide information about one or more of a patient's physiological parameters do not have the ability to connect to a data communications network for remote monitoring purposes. In this regard, these medical monitoring devices typically either are not used for remote medical monitoring, or, if any networking capability is provided for any purpose, these devices generally require interconnection to a separate device that provides an interface to the data communications for transmitting data to a predetermined location.

SUMMARY OF THE INVENTION

The present invention is based, in part, on the recognition that in order to provide medical information from an existing medical monitoring device across a data communications network, it is desirable that the monitored data be formatted prior to transfer such that a receiving device is able to properly output the monitored data. Additionally, for data network applications, it is desirable that remote display devices that are operable to receive data across a data communications network contain programs/protocols that are operable to recognize the formatted data received via the data network. As will be appreciated, due to the variety of medical monitoring devices existing, a display device may require a corresponding variety of display programs to display outputs produced by different medical monitors, or, even different models of the same monitor. In this regard, it has further been realized that it would be advantageous to provide an apparatus and method that allows for transferring patient data from an existing medical monitor over a data network to a remotely-located display device wherein the patient data from the existing medical monitor contains standardized display parameters. These standardized display parameters, such as display locations, display sizes, parameter definitions, allow an appropriately-configured display device utilizing a standard display program to receive and display the patient data from a multitude of medical monitoring devices without requiring specialized software for each monitoring device.

According to a first aspect of the present invention, an apparatus is provided for outputting patient data for receipt by a remote host. The apparatus includes a photoplethysmographic monitoring system, including: a sensor; an analog to digital converter; a memory; and a blood oxygen content generator for generating at least a first set of medical parameters related at least in part to blood oxygen saturation values. Further, the apparatus contains a processor in communication with the memory and/or blood oxygen generator that is operative to format the set of medical parameters into a formatted data set for transfer to a remote host. This formatted data set defines, in addition to each medical parameter in the set of medical parameters, at least one display layout for a remote host to utilize in providing a display output. Finally, the apparatus contains a network interface for transmission of the formatted data across a communications network to the remote host. As will be appreciated, the apparatus packages patient data from a medical monitor along with display information for receipt by a remote host. The remote host is then able to utilize the display information to produce an output of the medical parameters.

Though discussed in conjunction with the utilization of a photoplethysmographic sensor and monitor (i.e. pulse oximetry system), it will be appreciated that the inventive apparatus may be utilized with other medical monitoring devices. However, in the preferred embodiment wherein a photoplethysmographic sensor and monitor is utilized, the set of medical parameters produced by that medical monitor may include, inter alia, blood oxygen concentrations, perfusion index values, pulse rates, blood carbon dioxide concentrations, plethysmographic wave data, respiratory wave data, and blood concentration values. As will be appreciated, different pulse oximetry systems may produce different sets of medical parameters. Regardless of the type or number of these medical parameters produced by the pulse oximetry systems, the processor in communication with the pulse oximetry system is able to format the medical parameters for transfer to a remote host wherein at least one display output is provided for the medical parameters provided by that pulse oximetry system.

In a preferred embodiment, the apparatus will further include a user interface to allow a user to selectively provide additional information that may be included with the formatted data for transfer to the remote host. For example, the name of a patient, hospital, or doctor, may be included with the formatted data. Furthermore, date and time information may also be included.

The processor may format the data into any appropriate data format type for transfer to a remote host. As will be appreciated, the data format utilized may depend on the communication network utilized to interconnect to a remote host. For example, for communications with a remote host via a telephony network, the medical parameters may be formatted into an ASCII data format for transfer to the remote host. Furthermore, prior to transmission across a telephony network, the formatted data may be reproduced in an analog form for transfer. As will be appreciated, this may allow the data to be received by facsimile machine as well as processing platforms such as personal computers. Alternatively, when a data network such as the internet is utilized, alternate data formats may be utilized in formatting the data. In any case, the formatted data will include display layout information for use in providing an output of the monitored parameters. This display information may include, inter alia, layout information for graphical information associated with a set of medical parameters, as well as layout information for textual information associated with the medical parameters. This layout information may include, without limitation, location of the display on the output device, the size of display for the parameter of the output device, as well as color and font information for these outputs.

According to another aspect of the present invention, a system for formatting and transferring patient data for remote display is provided. The system includes a pulse oximetry monitoring device operable to produce at least a first set of patient data parameters and a processor configured to receive the patient data parameters. The processor is operative and format these patient data parameters into a byte stream format which contains at least a first set of data markers representing the patient data parameters and at least a second set of display markers representing display information associated with the patient data parameters. Last, the system contains a data network interface for transmission of the byte stream data via the data network to a remote display device which is configured to identify the first and second marker sets, and display the patient data according to the display information.

Utilization of a byte stream data format allows for increased flexibility in providing information over a data network. Particularly, the byte stream allows for inclusion of both binary and character information into an unstructured data stream (i.e., currently being produced as opposed to an existing data file) that may be easily formatted and sent across a data network. In a preferred embodiment, the Internet is the data network, however, it will be appreciated that other communication data networks may be utilized. When utilizing the Internet, the byte stream will be formatted into an Internet protocol prior to transfer to the remote display device. In any case, utilization of markers to represent display information and patient data information within a byte stream allows for the transfer of large amounts of data in a reduced format. For example, by utilizing a display marker indicating that a waveform graph is being sent (e.g., a plethysmographic wave) a graphing program supported by the remote display device can be initialized to receive graph data and reproduce the waveform. In this case, only (x, y) coordinates of waveform data points may need to be transferred to the remote display device as opposed transferring a complete data file including the waveform. As will be appreciated, this may result in reduced bandwidth requirements across the data network interface.

In a preferred embodiment, the byte stream further includes configuration information associated with the patient data parameters that is operative to configure a remote display device for displaying the patient data. In this regard, the configuration information may be provided prior to providing the data markers and display markers associated with the patient data parameters. This configuration information may include, without limitation, definitions of the patient data parameters that are to be sent to a remote display device via the data network, default display settings for each of patient data parameter to be sent, monitor identification information and/or patient information. Of particular importance, the default display settings will allow a remote display to configure its output to display the patient data parameters provided in the byte stream. In this regard, the default display settings may include the type of parameter to be displayed, such as textual or graphical, the location of each parameter to be displayed on the display output (e.g., x, y coordinates of a display output screen), the size of each display parameter for display on the display output, as well as the color and/or fonts utilized to display these parameters. The remote display device will contain a generic display program that recognizes the configuration information and provides processing support for displaying the data (e.g., a graphing program, audio programs, etc). The generic display program may be previously installed on the remote display device, downloaded from a server, or, provided by the processor of the present invention. The configuration information may be specifically designed to receive data from different pulse oximetry monitoring devices as different monitoring devices may provide different patient data parameters. However, the configuration information is formatted according to a standard protocol that provides standardized display contents that a remote display device can receive and display information from any monitoring device. Once the configuration information is provided to a remote display device, the byte stream containing the data markers and display markers is transferred to the display device via the data network. Upon receiving the data markers and display markers, the display device is able to decode and display the patient data parameters. That is, the individual parameters from the set of patient data parameters that are formatted into the data stream according to a predetermined formatting protocol are reproduced at the display device. Additionally, the display markers associated with the data parameters provide display settings for each individual parameter. That is, the display markers may include information regarding the type of parameter to be displayed allowing the remote display device to display the parameters in the appropriately configured portion of the display output.

In one embodiment, the processing system will be operative to receive multiple sets of patient data from the pulse oximetry monitor and contemporaneously format these sets of data into the byte stream format that includes data makers and display markers. In a further preferred embodiment, the processing system is operative to contemporaneously transfer the byte stream to a remote display device via the data network, allowing for near real time of remote medical monitoring, notwithstanding transmission times across the data network.

According to another aspect of the present invention, a method for formatting and transferring patient data to a remote display is provided. Initially, the method includes receiving patient data from a pulse oximetry monitor and receiving a request for that patient data from the remote display device, wherein that request is received via a data network such as the Internet. In response to receiving the request, display configuration data associated with the set of data parameters is provided for receipt by the remote display device wherein the display configuration data provides default display information for use by the remote display device in configuring an output display of the patient data parameters. Once the display configuration data has been made available to the display device, at least a first set of patient data parameters are provided to the remote display device for display thereon.

In a preferred embodiment of the method, the configuration data and the patient data parameters are embedded into a byte stream data format in which predefined markers are utilized to represent the data. As will be appreciated, a byte stream data format allows a convenient means for transferring unstructured files between processing platforms. That is, a byte stream is able to carry both textual information that may be provided from the medical monitoring device while also being able to carry numerical information such as patient data values (e.g., heart rate, profusion index, and blood oxygen levels) in a binary form. As will be appreciated, utilizing the markers in the byte stream allows for efficient transmission of patient data and/or display information associated with that data. Accordingly, this efficient representation may allow for reduced amounts of data to be transferred over the data network to a remote display device, thereby reducing bandwidth requirements. In this regard, the data network may utilize air interfaces (i.e. cellular, PCS) as well as fixed line data networks in providing a remote display.

The step of providing default display information for each patient data parameter may include, inter alia, providing information regarding the monitor type from which the patient data is provided, definitions of the patient data parameters provided by the monitor, and/or identification regarding a patient associated with the patient data parameters. The step of providing patient parameter definitions may also include providing display locations for use on display output, the display size of the particular parameter, display color, display font, and the parameter type (i.e., graphical or textual). This parameter definition information will generally be provided for each patient data parameter provided by the pulse oximetry system. This information is utilized by a remote display device to configure a display output, such as a display screen.

Once the configuration data has been transmitted to the remote display device, each patient data parameter from the set of data parameters is embedded into an individual package and provided to the remote display device via the data network. That is, each patient data parameter such as, for example, a heart rate, is embedded into a data package that provides information for use by the remote display device in identifying what the patient data parameter is so that it can be displayed in the appropriately configured portion of the display output. Furthermore, this data package may include information as to how the data parameter is packaged (e.g., 32-bit format) to allow for its proper display on the display output.

According to another aspect of the present invention, an apparatus for formatting and transferring patient data from a remote display is provided. The apparatus includes access protocol supported by a processing system for accessing a data input port associated with that processing system. The data input port may be in data communication with the pulse oximetry monitoring device or other monitoring device. That is, data output from a medical monitoring device is may be received at by the processing system through the accessed input ports. Further, the apparatus includes formatting protocol supported by a processing system for formatting data received through a data input port according to a predetermined format. Finally, the apparatus includes transfer protocol supported by the processing system for addressing the formatted data for transfer to a predetermined location via through a data network interface associated with the processing system. As will be appreciated, the apparatus may reside on a single processing platform such as a personal computer. That is, utilizing this apparatus a personal computer may interconnect to an existing medical monitoring device such as a pulse oximetry monitor and format data received from that monitoring device for transfer to a remote display device over a data network. Preferably, the data network will be represented by the Internet. In this regard, the processing system may further include a browser application for providing a network interface through the Internet.

BRIEF DESCRIPTION OF THE DRAWINGS

FIG. 5 shows an exemplary formatting scheme for including display information in a data stream prior to transfer to a display device.

FIG. 7 shows a process for receiving and formatting patient data from a medical monitor to include display information and transferring that formatted data via the Internet.

FIGS. 14A and 14B depict the facsimile report format of a device according to an embodiment of the present invention.

FIG. 15 depicts the internal printer report format of a device according to an embodiment of the present invention.

FIG. 16 depicts the remote host system report format of a device according to an embodiment of the present invention.

DETAILED DESCRIPTION

In the following description, the present invention is set forth with respect to certain illustrative embodiments for providing an apparatus and method a system that allows transferring patient data from existing medical monitors to a remotely-located display device over a communications network. A first illustrative embodiment of the present invention will be described in the context of utilizing the Internet to transfer patient data to a remote display device. A second embodiment will utilizes a public switched telephone network to transfer patient data to a remote display device, namely, a remote facsimile machine. However, will be appreciated that specific examples are included in the following description for purposes of clarity, but various details can be changed while remaining within scope the present invention. For example, the system is described herein in conjunction with transferring patient data from a pulse oximetry monitor and sensor to a remotely located display device, however, it is to be expressly understood that other monitoring devices may be used with the present invention.

Figure 1:
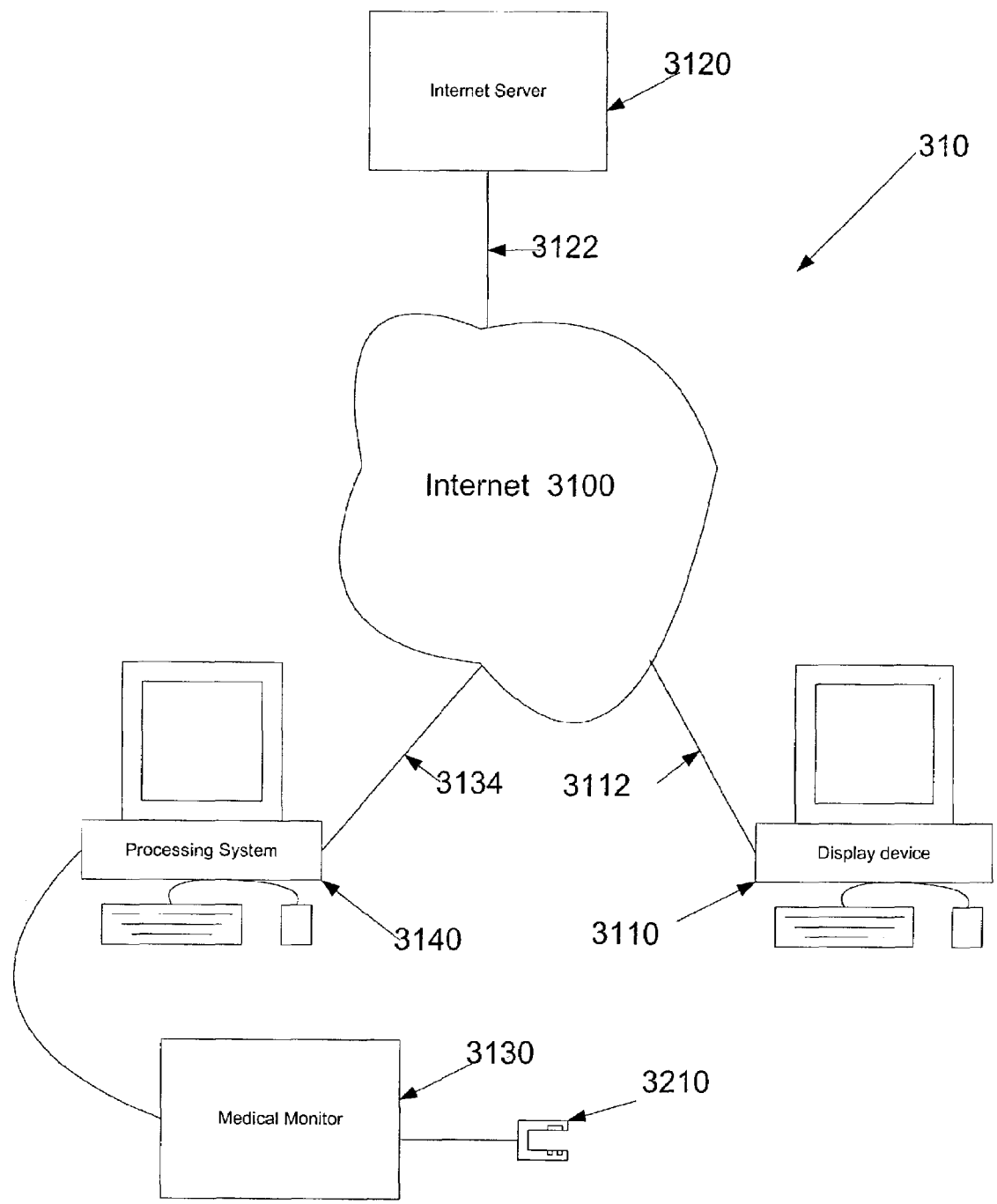
FIG. 1 shows a global data network in which the present invention may be implemented.

Referring to FIG. 1, a communications network is shown across which monitored patient data may be transferred for remote display. In this particular embodiment, the communications network is represented by the Internet, which is generally identified by the reference numeral 3100. As is well-known, the Internet 3100 is composed of a variety of network components including packet switched network systems and high-speed dedicated lines creating a network that connects millions of computers and/or Internet capable devices. The patient data transferring system 310 (hereinafter system) includes a point-of-care pulse oximetry monitor 3130 that utilizes a sensor 3210 for obtaining photoplethysmographic patient data relating to at least a first physiological parameter of an attached patient (not shown). The medical monitor 3130 is connected to a processing system 3140 that is configured to processes the patient data received from the monitor 3130 into a formatted data file or data stream, as the case may be, that includes display information for use by the remotely located display device 3110 to use when displaying the patient data, as will be more fully discussed herein. The processing system 3140 converts the formatted data file or stream into an Internet acceptable form (i.e., Internet protocol) for transferring this formatted data/stream to a predetermined destination via the Internet 3100. Additionally, the processing system 3140 also provides Internet access through a network interface communication link 3134 to transfer the formatted data over the Internet 3100. A display device 3110 is interconnected to the Internet via communications link 3112 that is operable to receive the formatted data via the Internet 3100 and display the patient data contained therein in accordance with the display information contained within the formatted data file/stream. The system may also include an Internet server 3120 for use in supplying appropriate protocol to either or both the processing system 3140 and/or the display device 3110. Additionally, an Internet server 3120 may be used by the display device 3110 in locating the processing system 3140, for storing formatted data from the processing system 3140 and/or providing display protocols.

The data links 3112 and 3134 interconnecting the display device 3110 and the processing system 3140 to the Internet 3100 may be of any type. For example, they may comprise a direct Internet communications link such as a local area network (LAN) that is directly interconnected to an Internet router, or they may, for example, comprise telephonic connections utilizing a modem to connect the processing system 3140 or display device 3110 to an Internet Service Provider (ISP). By utilizing this structure, the system 3010 components (i.e., medical monitoring device 3130, processing system 3140, display device 3110, and server 3120) may each be located in geographically distinct locations so long as appropriate communication links exist. For example, the display device 3110 and the processing system 3140 may be located in a geographically distinct areas, such as a medical facility and a patient's home, respectively. The Internet server 3120 may be located at or near the manufacturer of the monitoring equipment, allowing the manufacturer to easily maintain and/or update the server 3120, or may be operated by a network provider or a third party such as a hospital.

Figure 2:
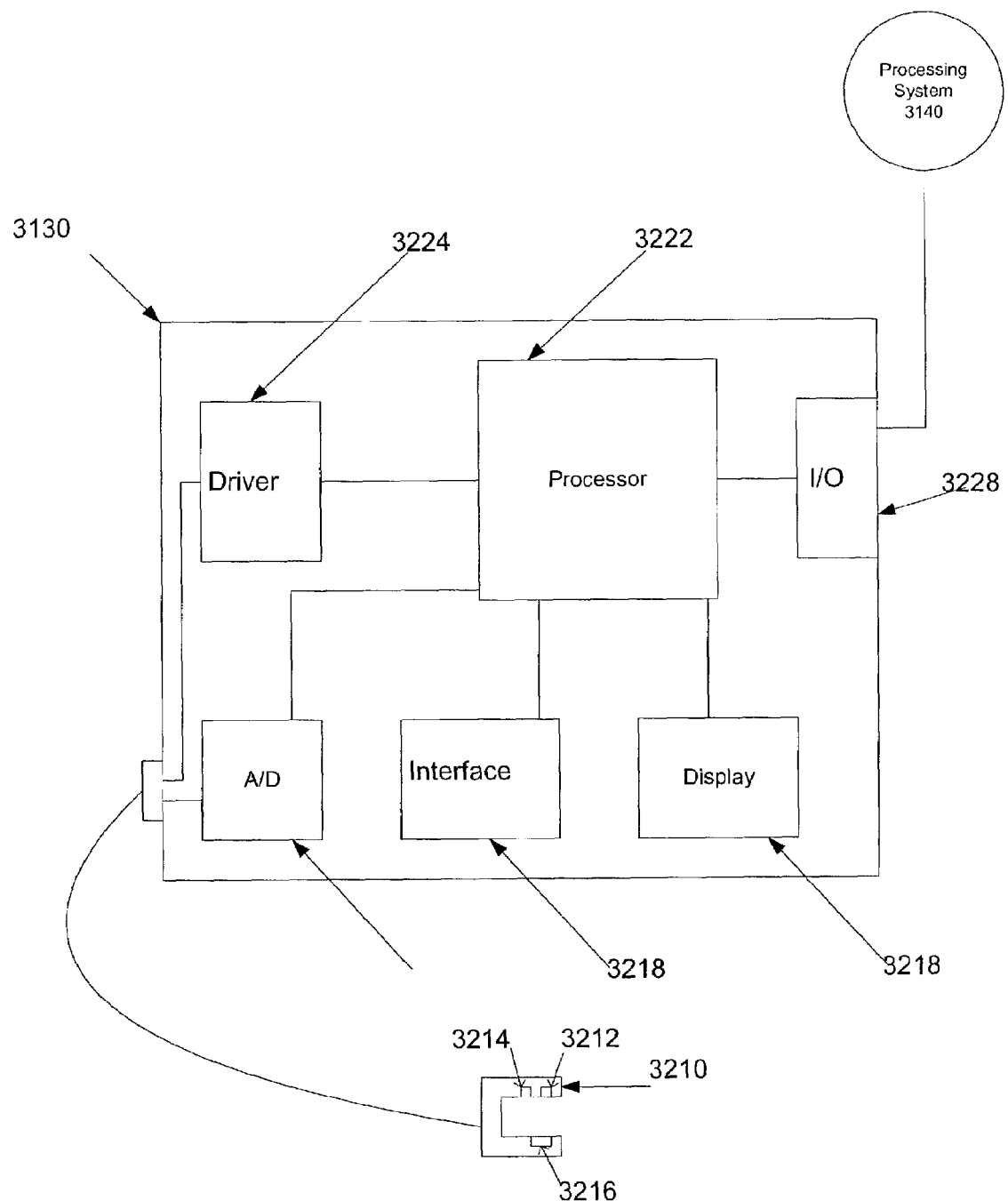
FIG. 2 shows an exemplary pulse oximetry monitor that may be utilized with the present invention.

FIG. 2 shows one embodiment of the pulse oximeter medical monitor 3130 that may be utilized with the present invention. As shown, the pulse oximetry monitor 3130 along with a pulse oximetry sensor 3210 are used to obtain patient data including one or more physiological parameters related to a patient's blood oxygen levels and produce an output of these data parameters. For example, the pulse oximetry system may produce a set of patient data that contains three parameters such as blood oxygen level (i.e., $SPO_2$), pulse rate, and a perfusion index as well as a time stamp indicating when these parameters were measured. The pulse oximetry monitor 3130 includes a display 3218, a user interface 3220 (which may be combined with the display 3218, e.g., a touch sensitive screen) for controlling the functions of the monitor 3200, an internal processor 3222, and a light driver 3224 for providing control signals to first and second light emitting diodes 3212, 3214 in the sensor 3210. The light emitting diodes 3212, 3214 apply optical signals to a portion of the patient's tissue and a photodetector 3216 detects the resulting optical signals passing through the tissue. The photodetector 3216 produces an analog signal indicative of the detected light signals. The monitor 3130 further includes an analog to digital converter 3226 for converting the photodetector signal into a digital signal for processing by the processor 3222. Finally, the monitor contains an input/output port 3228 (e.g., a serial port, a USB port, a IEEE 1394 port, etc.) for sending and receiving data to/from an attached device. As will be appreciated, the monitor 3130 may be a standard pulse oximetry monitor that can be utilized in a "stand alone" capacity when remote medical monitoring is not desired.

Figure 3:
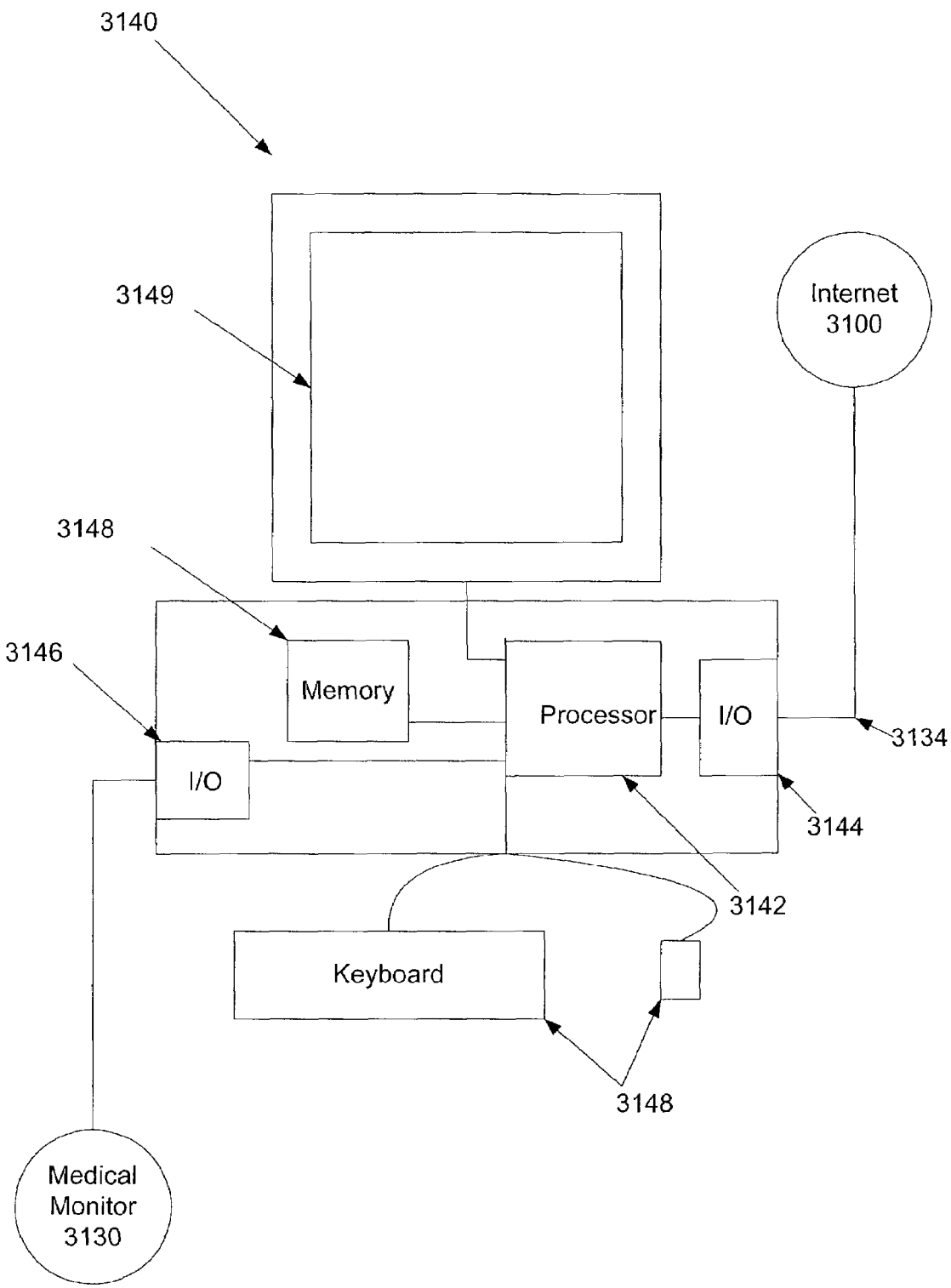
FIG. 3 shows a processing platform operable to receive patient data form the monitor of FIG. 2 and format that data for transfer over a global data network.

The input/output port 3228 of the medical monitor 3130 is interconnected to a first input/output port 3146 of the processing system 3140 (See FIG. 3). The processing system 3140 is configured to receive patient data from the monitor 3130 and format that data into a predetermined format that contains at a minimum default display information for each parameter contained within the patient data to allow a remote display device 3110 to display the patient data according to the default parameters. As shown, the processing system 3140 comprises a personal computer PC that is able to support the necessary protocol for the receiving and formatting functions required by the present invention. Accordingly, the processing system 3140 includes an internal processor 3142 and a memory structure 3148, a user interface 3147, a display 3149, and a second input/output port 3144 for connecting the processing system 3140 to the Internet 3100. Though illustrated as a PC, It will be appreciated that any processing system that provides the required functionality may be utilized.

The processing system 3140 supports data collection module or "protocol" that allows the processing system 3140 and medical monitoring device 3130 to communicate. This data collection protocol is stored in the system's memory 3148 and provides instructions that allow the processing system 3140 to access its input port 3146 and receive patient data from the attached medical monitoring device 3130. As this protocol accesses the system's input port 3146, it will generally be platform dependant and may comprise an executable program or, for example, a Java applet downloaded from the Internet. In any case, a user locates and installs appropriate protocol for the processing system 3140 utilized. However, any platform (UNIX, Windows, etc.) that supports appropriate protocol may be utilized for the processing system 3140. Further, this data collection protocol will generally be medical monitor specific since different medical monitors produce patient data relating to differing physiological conditions as well as producing outputs in varying forms (i.e., text, binary, etc). Therefore, the data collection protocol will be individually tailored for each medical monitoring device.

In a basic form, the data collection protocol will allow an existing monitor 3130 to be interconnected with a processing system 3140 such as a PC, so the processing system 3140 can receive patient data in the form it is received from the monitor 3130. The processing system 3140 may then package the received patient data for transfer to a remote display device 3110 using, for example, the Internet 3100. In this case, a remote display device 3100 would support a specific display protocol or software associated with the monitor 3130 to display the patient data. In the preferred embodiment of the present invention, the data collection protocol supported by the processing system 3140 formats the received patient data into a data stream that includes display information that allows the data to be displayed by a remote monitoring device using a generic display protocol (i.e. non-monitor specific), as will be discussed herein.

Once the patient data is received and/or formatted by the processing system 3140, that data is transferred via the Internet to a predetermined destination such as a remote display device 3110 or data storage facility such as server 3120. In this regard, the processing system 3140 contains a second protocol for converting the patient data into an appropriate format for transfer across the Internet 3100. This second protocol may also be stored in the processing system's memory 3148 and may comprise an Internet browser application. The data is packaged such that it conforms to an Internet open standard protocol. In the present embodiment Transmission Control Protocol (TCP/IP), which allows two Internet "hosts" to form a connection and exchange data is utilized. The TCP protocol packages the formatted patient data into a plurality of packets which are addressed and sent to a requesting client. As will be appreciated, the Internet 3100 is a packet switching network in which data files are divided into packets before they are sent. Each packet contains a header that contains a variety of information, such as the order in which the packets should be reassembled as well a body of data. Each packet is then transmitted individually in an IP envelope containing addressing information informing the Internet 3100 where to send the data. As will be appreciated each IP envelope can utilize differing routes to deliver the packets to their destination. Once all the packets forming a message arrive at the destination, they are recompiled into their original order. Though the data packets do not have a guaranteed arrival time and the packets corresponding to a single message may be received out of order, the TCP protocol is responsible for verifying the correct delivery of the data. That is, TCP protocol will detect errors and/or lost data and trigger retransmission until the data is correctly and completely received. Though discussed in conjunction with utilizing the Internet 3100, another embodiment of the present invention may be implemented utilizing a direct connection where the processing system 3140 and display device 3110 are connected to one another utilizing a dedicated line (e.g., a phone line of a telephony network). In this case, another protocol, such as UDP, may be utilized to transfer the patient data between the processing system 3140 and remotely located display device 3110.

In the present embodiment, the data collection protocol supported by the processing system 3140 formats the patient data received from the medical monitoring device 3130 into a special data file or data stream containing display information according to a predetermined formatting scheme. Once the patient data is "encoded" according to the predetermined formatting scheme, a properly configured remote monitoring display device 3110 can receive the formatted data file/stream and display the patient data contained therein in accordance with the encoded display information. That is, the data collection protocol embeds the received patient data into a display format file according to a predetermined formatting scheme prior to that display format file being transferred over communications network (i.e., the Internet) to a remote display device 3110. This remote display device supports a generic display protocol "decodes" the display format file and displays the data according to the default display settings contained therein.

Figure 4:
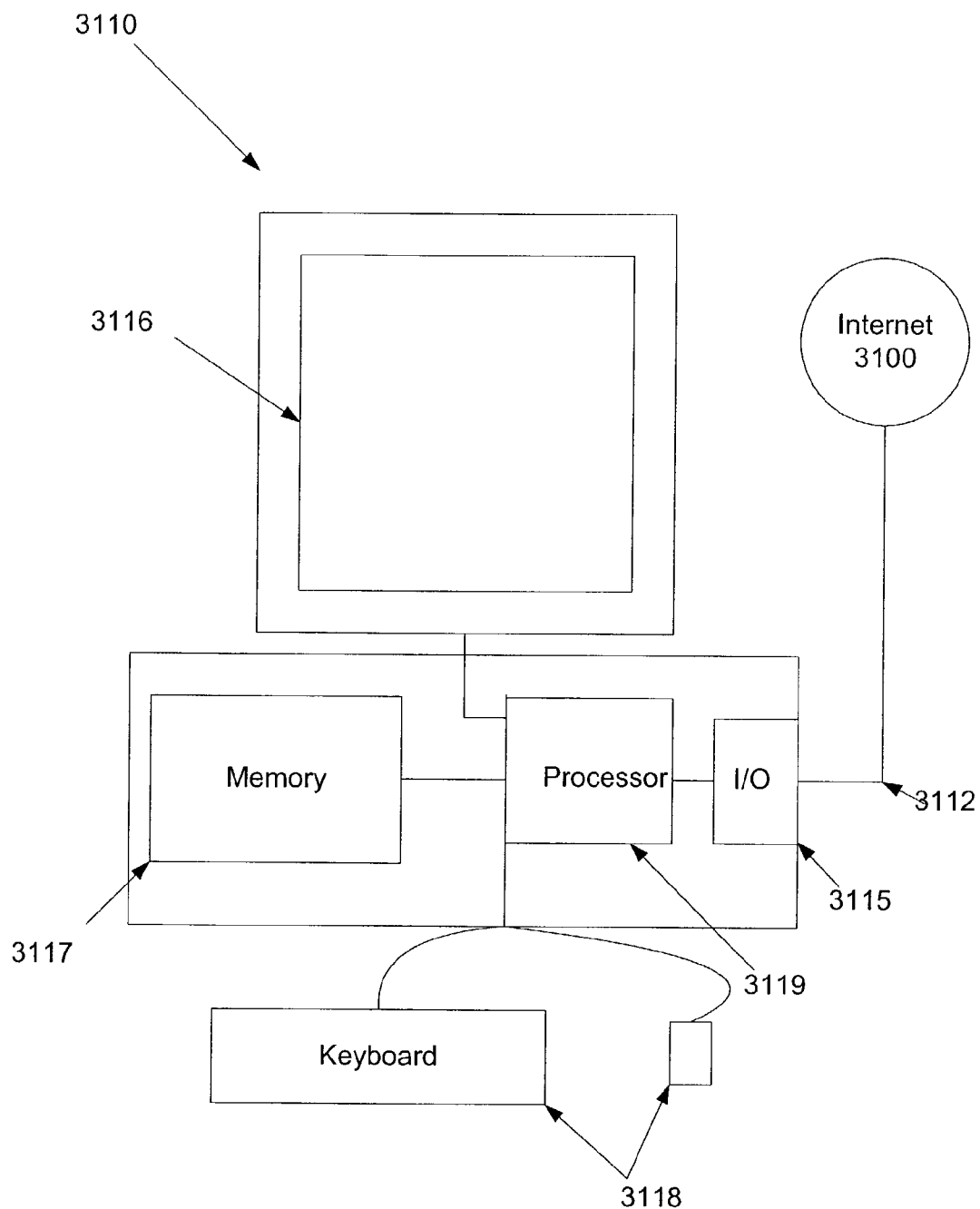
FIG. 4 shows a display device operable to receive a data stream from the processing system of FIG. 3 and display that data according to display information contained within the data stream.

As shown in FIG. 4, the display device 3110 utilized with the present invention is a computer system having access the Internet 3100 via communication link 3112. The computer system contains a display 3116 and a user interface 3118 comprising a keyboard and mouse. The computer system also contains a processor 3119 that supports a web browser application such as NETSCAPE or IEXLORER, stored in an attached memory 3117. The browser application allows the display device 3110 to communicate over the Internet 3100 using, for example, hypertext transfer protocols (HTTP) as well as its underlying TCP/IP protocols. The browser enables the computer system to receive and display information from the Internet 3100 through an input/output port 3115. Though described in the context of a personal computer, the display device 3110 may be embodied in a variety of other devices that enable a user to access and receive data via the Internet 3100. Such devices include but not limited to, cellular telephones, pagers, personal digital assistants or any other device that provides Internet access and has some sort of display device and user interface. The display device 3110 also supports a display module or "display protocol" that allows the display device 3110 to identify the patient data within the formatted data file/stream and display that patient data in accordance with the display information contained therein, as will be discussed herein.

The pulse oximetry device 3130, as shown, produces a text stream indicative of its current parameter status. In particular, the oximetry device produces a text stream having time stamp, the blood oxygen level, a pulse rate, and a profusion index. This text stream may be produced, for example, every two seconds. In this regard, the data collection protocol of the processing system 3140 will continuously receive this textual data stream from the pulse oximetry device 3130 and contemporaneously format this data into a formatted data stream containing display information according to a predetermined formatting protocol.

As shown in FIG. 5, an exemplary formatting protocol is illustrated. The patient data may be encoded into a data file/stream containing five separate sections. In particular, a first section may provide monitor information including, but not limited to, the type of the medical monitor, its model number, its serial number, and/or the data collection software program name and/or version. A second section may contain parameter definition that define each parameter contained within the patient data received from the monitor 3130. These parameter definitions may include, inter alia, a parameter identification tag, a parameter name, the data type such as integer, floating point, character text, Boolean, graphical picture, etc. Further, the parameter definitions will contain the size of the data or the number of bytes each data point may take up, the expected frequency of transmission and the maximum and minimum possible values for the particular parameter. A third section will define the default parameter display settings for use by a generic display protocol in reproducing the patient data parameters on a remote display device 3110. These default settings may be ignored or modified by a display program that has been so configured by a user. For example, a foreign user may modify the text default setting to change labels to another language. Alternatively, a user who is not interested in a particular parameter may have that parameter deleted from their display. Regardless, each default display setting will contain a parameter I.D. and/or label, screen locations of the labels, and text sizes as well as foreground and/or background colors for the labels. In addition, each parameter will contain a current display value or, in the case of plotted data, a graphical trace over time. For graphical traces, additional information will include the amount of time to display, scale, trace color and/or point style. Finally, the default parameter display settings may include a tag that allows a user to modify the display settings, that is, one or more of the parameters may not be user adjustable.

A fourth formatting section contains patient specific information such as a patient's name, an encrypted password that allows a remote user to have access to the remote data, a physician's name, a hospital name and/or a time stamp indicating the time the data was recorded. Section 4 is optional. Furthermore, it will be appreciated that Sections 1–4 are "set-up" or configuration sections and accordingly, these sections may only be provided upon initial connection of the processing system 3140 to a remote display device 3110. That is, these initial sections 1–4 may initially be sent to a remote display device 3110 to configure that display device's display protocol to display data from a monitor 3130. Additionally, the processing system 3140 may be configured to allow multiple display devices 3110 to receive the patient data. In this regard when each display device 3100 initiates contact, set-up information is sent. Once the default display settings are sent, a fifth section containing data packets will be sent to "fill in" the set-up display. In the case of the pulse oximetry monitor 3130, each data packet will contain a time stamp, parameter I.D. for each of the three noted parameters, as well as a data value associated with each of the noted parameter (see FIG. 5). In this regard, this fifth section may be sent on a continuous basis to a remote display device 3110, which may then refresh its display to show the updated values. For example, FIG. 16 shows a display on which a series of updated formatted data sets are remotely displayed.

Figure 6:
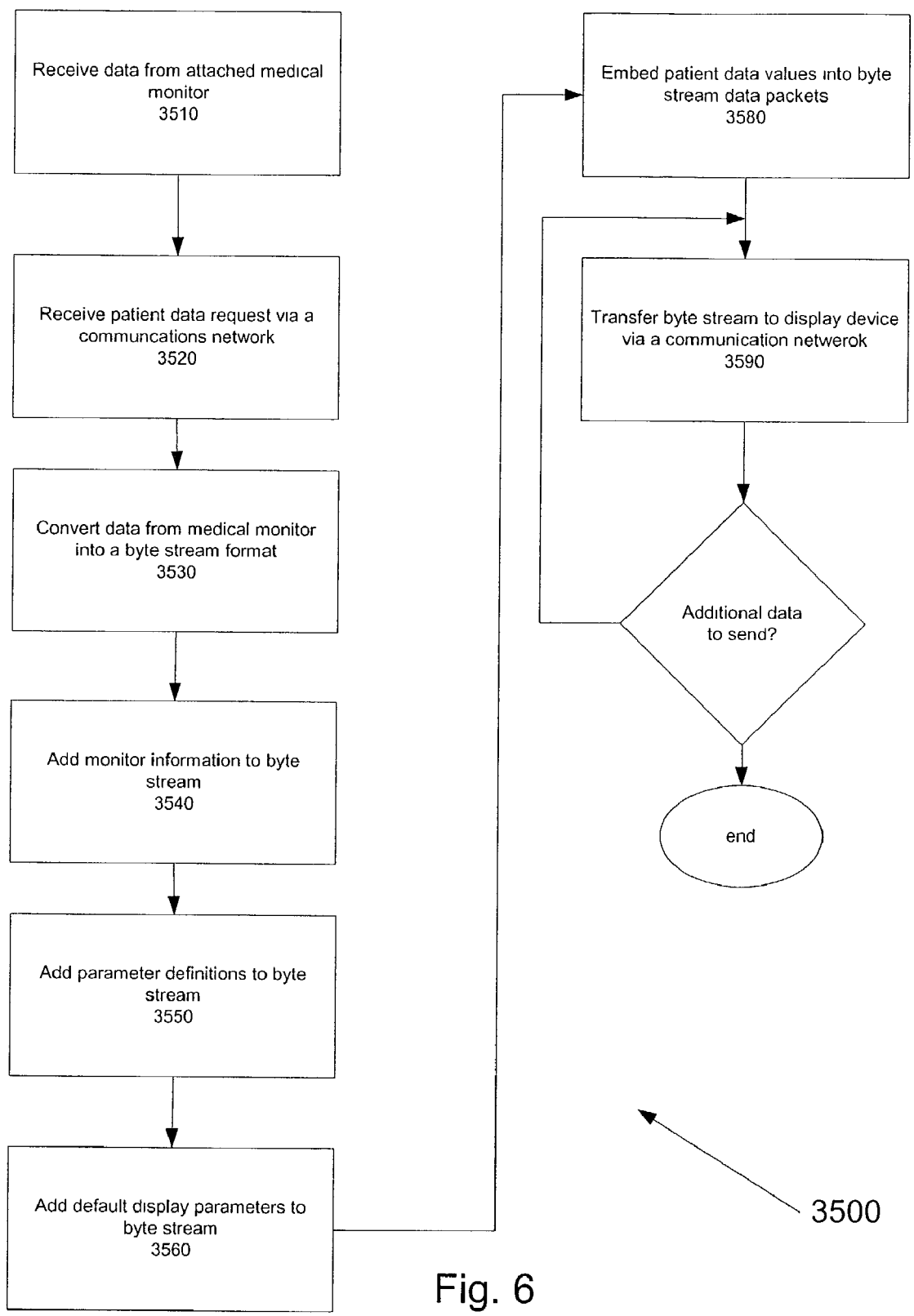
FIG. 6 shows an exemplary byte stream containing display information and patient data.

FIG. 6 shows an exemplary process (3500) of formatting patient data received from a medical monitoring device 3130 into a formatted data stream that includes display information. In this embodiment, a text output from a pulse oximetry monitoring device 3130 having the form of:

":04:36:14 SpO₂=94 PR=60 PIr=4.34"

is produced. This outputs shows the time of the monitor reading, a blood oxygen level (SpO₂), a pulse rate and the patient's perfusion index. This textual output is produced every two seconds, therefore the current process (3500) details creating a formatted data "stream" containing display information that allows the data stream to be "self-supporting" for remote display.

Initially the data collection protocol supported by the processing system 3104 receives (3510) the above-noted textual output from the pulse oximetry monitor 3130. When the processing system 3140 receives (3520) a request for patient data, which may be delivered via the Internet 3100, the data collection protocol, which is specifically designed for use with this pulse oximetry monitor 3130, converts (3530) the textual data stream into a byte stream format according to the predetermined formatting protocol. A byte stream data format is especially desirable for use due to its ability to convey both binary and character information. That is, any textual information from the monitor 3130 may be conveyed as character information while configuration markers (as will be discussed herein) may be conveyed as binary terms. The byte stream format is particularly useful due to its flexibility if transferring various data forms.

An exemplary byte stream formatting protocol is shown in FIGS. 7a and 7b, where the left hand column shows the byte stream data and the right hand column provides explanatory descriptions for purposes of clarity; however, it will be appreciated that, in actual operation, the right hand column will not be created nor transferred to a remote display device 3110. Upon receiving (3520) the request for patient data from a remote display device 3110, the processing system 3140 converts (3530) the patient data parameters (i.e. SpO₂, PR and PI) from the pulse oximetry monitor 3130 into a self-supporting byte stream in several sub steps. Initially, the data collection protocol adds set-up information to the beginning of a byte stream to allow a remote display device 3110 supporting the proper display protocol to configure itself to display the patient data. In particular, the data collection protocol adds (3540) monitor specific information to the byte stream as shown in section 1 in FIG. 7a. As shown, the data contained in quotes is ASCII text that may be used for labels in the display while the numbers are binary markers or "code" that identify the various display related values. These markers allow the display device 3110 to identify information that follows within the byte stream.

Secondly, the data collection protocol adds (3550) parameter definitions to the byte stream for each patient data parameter produced by the pulse oximetry monitor. As shown in section 2 of FIG. 7a, a first marker in the byte stream indicates that a parameter definition follows; a second marker (0,0) indicates the parameter's identification; a third marker indicates the parameter's name; a fourth, the data type; a fifth, the expected frequency; and the sixth and seventh markers indicate the minimum and maximum values for a given parameter. As will be discussed herein, the display protocol supported by the display device will utilize these definitions to properly display the patient data.

Third, the data collection protocol adds (3560) default display settings for each parameter produced by the pulse oximetry monitor 3130. Markers are utilized to indicate what settings are utilized in displaying the parameters. These markers define where and how these parameters will be displayed. As shown in FIG. 7a, the x and y coordinates for the parameter label as well as the x and y coordinates for the current display values are defined as well as, inter alia, text size and colors for these displayed parameters. As will be appreciated, other display parameters could be included. A fourth set-up section is added (3570) to the byte stream includes patient information and/or a password to restrict access to authorized remote users. As will be appreciated, in order to include patient data, the data collection protocol

3500 may prompt user inputs through the processing system's interface. Finally, a set of patient data packets are added (3580) to the byte stream. That is, each parameter value from the received data stream (3510) is embedded into a packet that has a time, (see FIG. 7b) a parameter identifying marker, and data type marker. As shown, the $SpO_2$ value of 94.0, it is embedded into the byte stream in IEEE 32 bit format.

After, or, contemporaneously with the set-up information and first set of patient data packets being formed into a byte stream format, the resulting byte stream is transferred (3590) to the remote display device in the manner described above. Additionally, each time the pulse oximetry device produces an updated patient data output, the parameter values are embedded (3580) into a set of data packets and transferred (3590) to the display device until the protocol is instructed to stop.

Figure 8:
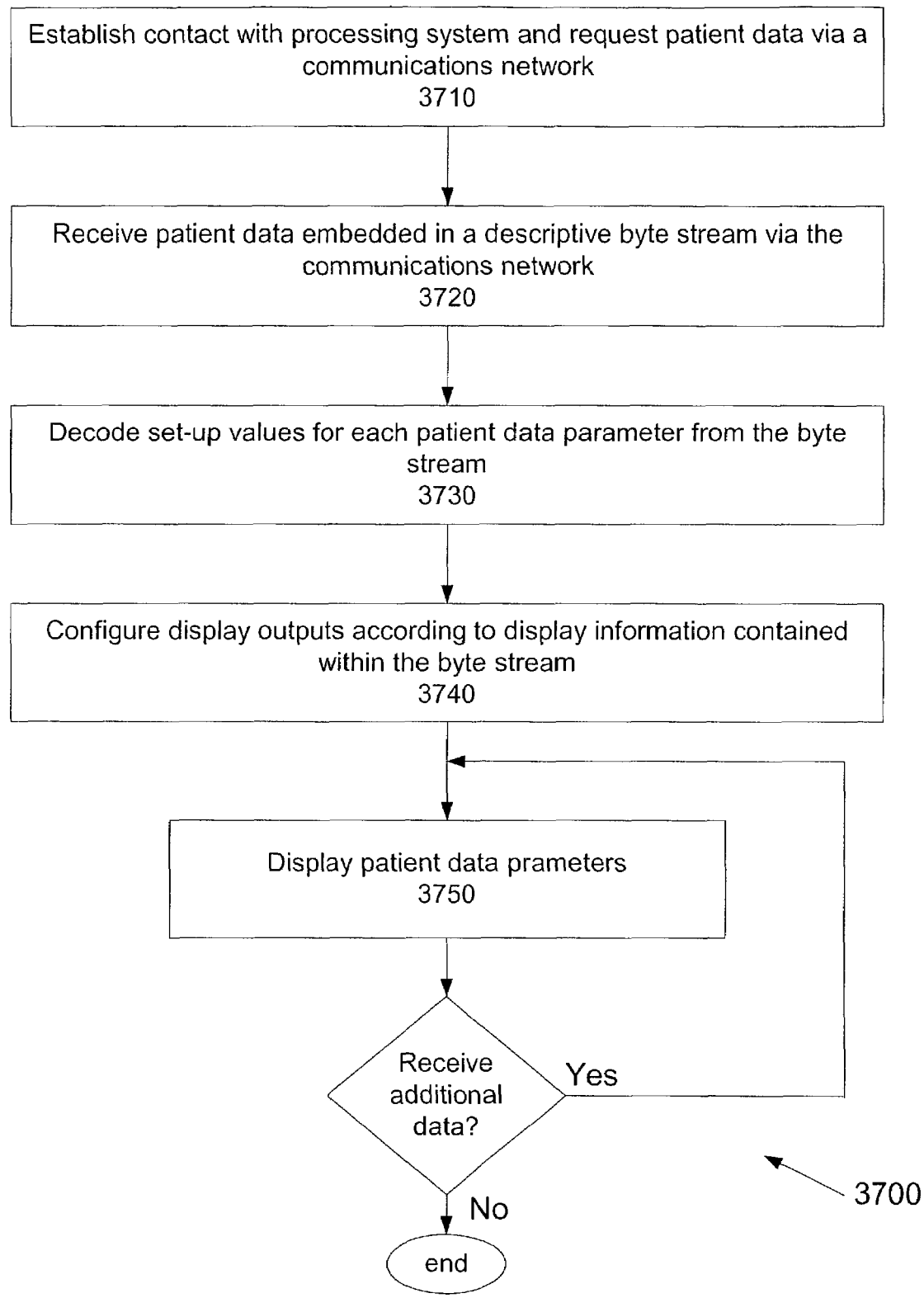
FIG. 8 shows a process for receiving formatted patient data containing display information via the internet and displaying that patient data according to that display information.

Unlike the data collection protocol which is medical monitor specific, the display protocol may be a generic program operable to decode and display patient information from a variety of medical monitoring devices. That is, while each medical monitoring device may produce a different set of patient data parameters, each of these parameters will be formatted according to the predetermined formatting scheme which the display protocol is able to recognize and display. In this regard, the display protocol simply prints or plots the data it receives according to this predetermined formatting scheme, thereby allowing the display protocol to display patient data from a variety of medical monitoring devices. As shown in reference to FIGS. 7, and 8 a process (3700) for receiving formatted patient data via a global data network is described. Initially, the display device 3110 establishes contact (3710) with the processing system 3140 and requests patient data. Accordingly the formatted byte stream including the patient data is received (3720) by the display device 3110 via the Internet 3100. Upon receiving the formatted byte stream, the display protocol supported by the display device 3110 decodes (3730) the set-up information contained in the first four sections of the byte stream. That is, the display protocol reads the byte stream according to the markers and separates the data contained therein. Accordingly, the display protocol configures (3740) the display device 3110 according to the default settings contained within the byte stream. For example, As shown in FIG. 16, header information 801, patient information 802, as well as a date 803 and their display locations are provided in the first four sections of the formatted data stream to allow proper remote display. As noted, these default settings may be adjustable by, for example, adjusting a settings menu associated with the display protocol.

Once the display device is configured (3740), the data values for each parameter contained within the first set of data packets are displayed (3750) in the appropriately configured section of the display device's display. In this regard, the display protocol will generally include a graphing sub-routine to allow for graphical data to be plotted on the display device as well as supporting textual values supplied by the byte stream. In addition, other sub-routines, such as an audio player, may be incorporated to support additional types of data. The display protocol will update the displayed values each time a new set of data packets is received.

In a variation of the first embodiment of the present invention, the data packets will be received (3720) and displayed (3750) contemporaneously with their production. That is, as the updated parameters are produced by a medical monitoring device, they are delivered to the processing system 3140, formatted according to the predetermined formatting scheme and transferred to the display device 3110 where they are displayed contemporaneously with their production, notwithstanding processing and transferring times.

Referring to FIG. 1, it will be noted that the server 3120 comprises a dedicated Internet server having internal processors and databases. The internet server 3120 is accessible via the Internet 3100 by both the processing system 3140 as well as the display device 3110. In a preferred embodiment of the system 3010, any data collection protocols and display protocol required allow remote medical monitoring in accordance with the present invention are databases at the server 3120. In this embodiment, a medical facility may download the data collection protocol for the medical monitoring device they are utilizing. Accordingly, a remote user may also access the database and download the generic display protocol to display patient data produced by a medical monitor 3130 and formatted by a data collection protocol.

In order for the display device 3110 to access and display patient data from the medical monitor 3130 via the Internet, the attached processing system 3140 must have some sort of Internet address that the display device 3110 can locate and contact. One solution is for the processing system 3140 to use a fixed IP address that is registered with a domain name server (DNS) database 3186 at the server 3120. However, this approach creates a problem of utilizing the processing system 3140 to connect a medical monitor 3130 to the Internet from a different location upon, for example, movement of the patient to a new location. Therefore, it is preferable to utilize a dynamic naming scheme that allows the processing system 3140 to be readily located when moved to new locations. Preferably, Dynamic Host Configuration Protocol (DHCP), which is a protocol for assigning a dynamic IP address to devices on a network, is used to identify the processing system 3140. With dynamic addressing, a device can have a different IP address every time it connects to the network. Dynamic addressing simplifies network administration because software at the server keeps track of the IP addresses rather than requiring an administrator to manage the task. This means that an Internet device (e.g., processing system 3140) can be added to the network without manually assigning it a unique IP address. By using DHCP, the processing system 3140 registers with what may be called a dynamic domain name system (DDNS) server 3120 each time it is connected to the Internet 3100.

Regardless of the registration method utilized, the processing system 3140 provides a unique identification means. One solution is to utilize the serial number of the medical monitor 3130 or the processing system 3140. For example, the processing system 3140 may register under the name "MONITOR_SN.DNS . . . " where MONITOR is the type of attached monitor, such as a pulse oximeter, PO, and DNS is the name of the server currently supporting this unit. An example of the dynamic name might be "PO_12345.6ST_Henrys.com, where St. Henrys is a hospital server. Regardless what system is used, the important aspect is that the server 3120 contains communication information, such as a URL, for use in contacting a selected medical monitor 3130 through its processing system 3140.

In the second noted embodiment, the present invention enables the user of a photoplethysmographic system to send collected photoplethysmographic data from the system to a remotely located facsimile machine thereby providing a formatted hard copy printout of the photoplethysmographic data without the use of auxiliary computing devices, such as a personal computer or central monitoring station. Thereby, useful photoplethysmographic data, such as $SpO_2$ levels, pulse rates, and pulsatility values can be transmitted in a useful format from any location to a remotely located medical practitioner using standard telecommunications equipment. Data may also be sent directly to a remote host system, such as a personal computer, through the modem, or directly downloaded to a personal computer through an RS232 interface. In addition, the present invention will automatically answer an incoming call from a personal computer, and allow the personal computer to access the photoplethysmographic data. An optional internal printer can provide on-demand hard copy output of the collected data.

The monitoring apparatus described herein as the preferred embodiment is a pulse oximeter instrument which measures the oxygen saturation of the arterial blood of a patient. The pulse oximeter instrument operates by illuminating the arteriolar bed of a perfused appendage, ear lobe, or nasal septum of the patient with light from light sources characterized by spectra having distinct center wavelengths. The center wavelengths are selected so that the light emitted by one light source is highly absorbed by oxygenated hemoglobin contained in the arterial blood, while the other is selected with respect to its absorbency by deoxygenated hemoglobin. The pulse oximeter instrument then measures the magnitude of the light that passes through the illuminated tissue. The pulsatile component of the light output from the tissue is used to determine the oxygen saturation of the arterial blood flow.

Figure 9:
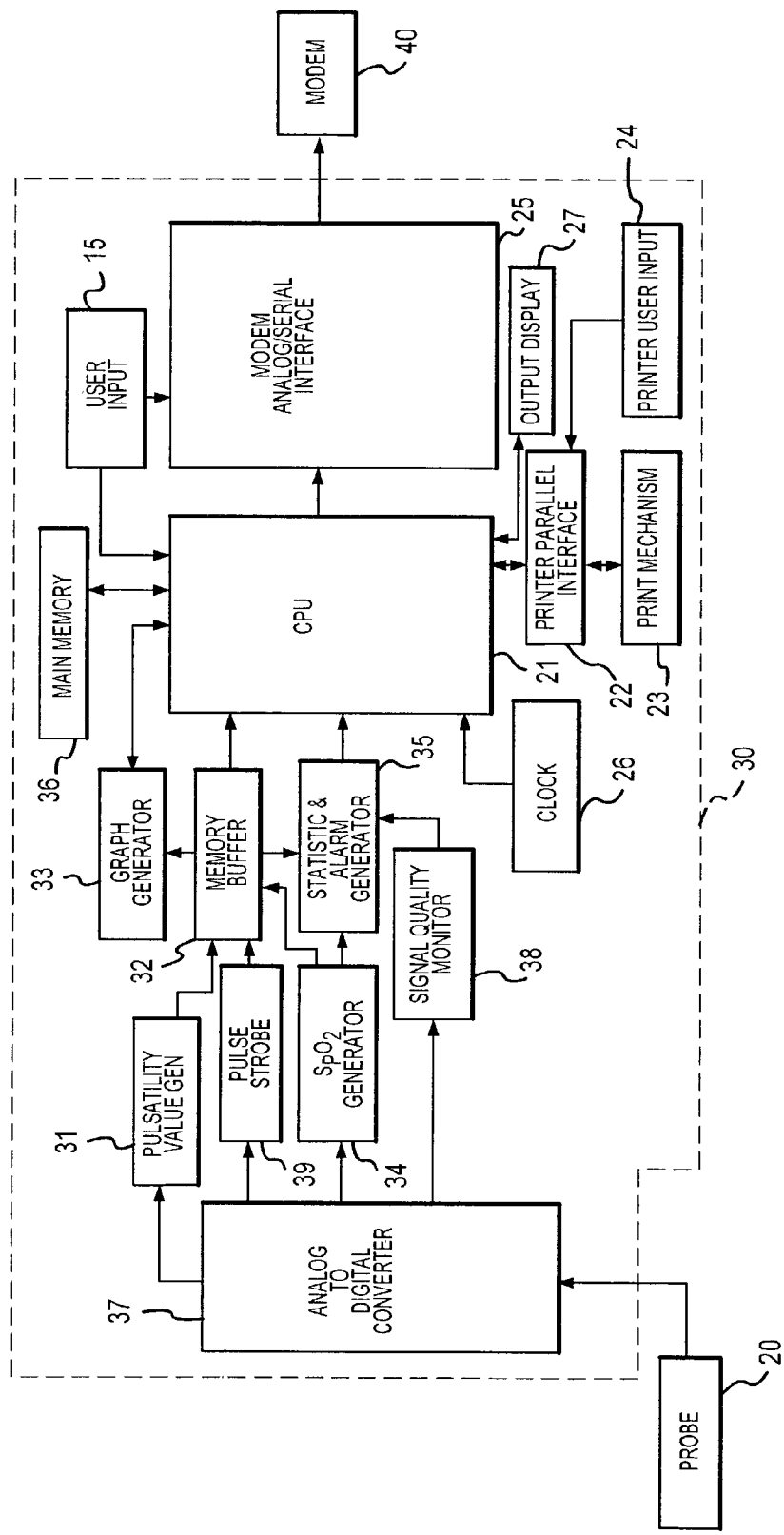
FIG. 9 is a functional block diagram of one embodiment of the present invention in which the formatted data is directed to an external modem or to an internal printer.
Figure 10:
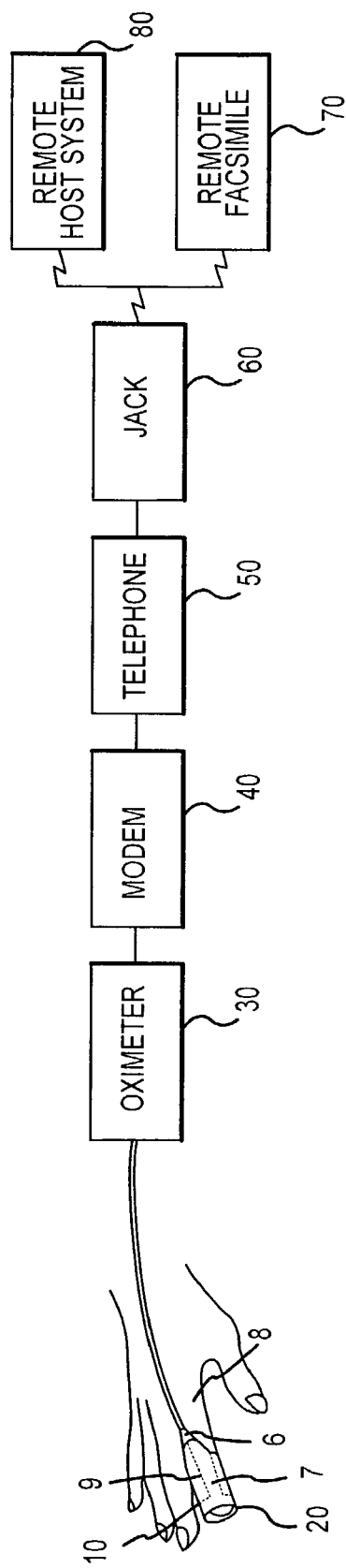
FIG. 10 is a block diagram of the embodiment of FIG. 9 further depicting functional components of the system of FIG. 9.

Referring to FIGS. 9 and 10, a probe 20 containing a plurality of light sources 9 and 10, such as LED or laser diodes, and a photo detector 7 is attached to an appendage of the patient, such as a finger 8. The appendage is rich in arterial blood flow so that the light transmissivity of the arterial blood, and thereby the oxygen saturation thereof, can be directly measured. The light sources 9 and 10 and photo detector 7 may, alternatively, be placed on the ear lobe or nasal septum of the patient. The output signal produced by the photo detector 7 is transmitted via cable 6 and is processed by the pulse oximeter instrument 30, producing a numeric value indicative of the oxygen saturation of the arterial blood. It is a collection of these oxygen saturation levels ($SpO_2$ levels) over time that is transmitted to a remote location or retrieved from a remote location or printed out on an internal printer.

The functional block diagram of the pulse oximeter instrument 30 of FIG. 9 provides a description of the internal processing necessary to provide a complete facsimile data format output to modem 40 and to remote facsimile 70, to provide an ASCII data format output to modem 40 and to remote host system 80, and to provide an ASCII data format output to print mechanism 23.

Raw input data from probe 20 is converted to a digital representation by analog-to-digital converter 37. The digital data set representing the output from photo detector 7 of probe 20 is then used by the software internal to the pulse oximeter instrument 30 to calculate the $SpO_2$ level of the patient's blood in a well known way. For instance, the techniques discussed in U.S. Pat. No. 5,503,148 issued to Polonge et. al., hereby incorporated by reference, may be used for calculating $SpO_2$ levels.

The digital data set from the analog-to-digital converter 37 is used by the $SpO_2$ generator 34 to generate $SpO_2$ saturation levels at specific time intervals of at least every six seconds. The $SpO_2$ saturation levels generated by the $SpO_2$ generator 34 are then forwarded to a memory buffer 32 where a time-tagged series of $SpO_2$ blood saturation values is stored for later output to central processing unit 21 and on to main memory 36, modem analog/serial interface 25, output display 27, and printer parallel interface 22, and for use by graph generator 33 and statistic and alarm generator 35. Output display 27 is typically a combination of an LED display and an LCD display, but could be one or the other only. Photoplethysmographic waveform and trend data are easily displayed on the LCD type display. Saturation and pulse rate values and alarm indicators are readily displayed on the LED type display.

The $SpO_2$ saturation levels generated by the $SpO_2$ generator 34 are forwarded from memory buffer 32 to a statistic and alarm generator 35 where a set of statistical characteristics for a data set are defined for the buffered set of data. For example, a histogram may be generated as well as a breakdown by range of the amount of time the $SpO_2$ level was within certain ranges. Other statistical characteristics such as the highest and lowest $SpO_2$ levels and durations for each of the high and low levels for a given set of data can also be generated by the statistic and alarm generator 35. Examples of alarms which can be generated by the statistic and alarm generator 35 include "Low $SpO_2$", "High $SpO_2$", "No Sensor" and "Sensor Off" warnings. These latter two warnings are generated by the data emerging from the signal quality monitor 38.

Signal quality monitor 38 receives data from the analog-to-digital converter which is indicative of the quality of the input data signal. The quality of the signal can be a measure of the signal to noise ratio, intensity and/or frequency of motion artifacts, or other measure of the credibility of the input data, regardless of the signal strength. The signal quality monitor 38, in response to the received data, produces one of a plurality of drive signals to generate an indication of the quality of the input data signal in order to determine if an alarm such as "No Sensor" or "Sensor Off" should be displayed to the user.

There are other characteristics of the input signal received from probe 20 that are of interest to the user of the pulse oximeter 30, such as the patients' pulse rate and pulsatility value. Data from analog-to-digital converter 37 is also supplied to pulse strobe 39 to provide a time-tagged pulse value for the patient which is then stored in memory buffer 32 for later transfer through central processing unit 21 to specific memory locations in main memory 36. The data will later be used by modem analog/serial interface 25 and printer parallel interface 22. The statistic and alarm generator 35 also uses the set of pulse values to develop a high and low pulse statistic and rate duration as well as high and low pulse alarms. Data from analog-to-digital converter 37 is also forwarded to a pulsatility value generator 31 where the pulsatility value is generated according to one or more known methods, including, but not limited to, percent modulation.

Graph generator 33 provides a bar graph or other graphical representation of photoplethysmographic data which can then be stored in main memory 36 and formatted for transmission to the remote facsimile via modem 40. Internal clock 26 is used to time-tag data and provide the date of data collection, the time the data collection began, and the duration of the data collection.

User input 15 provides a mechanism for the user, generally, the nurse, home-care aide or physician, to input data regarding the patient and the time and date of the photoplethysmographic study. Additionally, user input 15 permits the user to select the duration of the study, to select the format of data to be displayed on output display 27, to select modem characteristics, and set up pulse oximeter 30 for transmission of data via modem 40 or in response to receiving a call from remote host system 80. User input 15 may comprise one or more of the following input devices: touch-sensitive screen, keyboard, touch-pad, mouse, trackball, joystick, or axially actuatable rotary dial (for example, as disclosed in U.S. Pat. No. 5,627,531 to Reichert et al., and hereby incorporated by reference). In an alternate embodiment the user input 15 is external to pulse oximeter 30 and communicates through the standard RS232 port found on most pulse oximeters. In this alternate embodiment user input 15 may be a personal computer or some other communication device having a user interface and a serial communication port.

Print mechanism 23 can provide on-demand hard copy output of the data collected by probe 20 and processed by pulse oximeter 30. Printer mechanism 23 is typically a thermal single column dot matrix printer. Printer user input 24 is only active when waveform data or trend data is being displayed on output display 27.

The user may select one of several options with printer user input 24. The user may select to print out real time data while monitoring the patient. The real time data may be printed out in $SpO_2$ format or PI™ format in either six second or thirty second intervals. Selecting a summation option during real time printing immediately stops the real time printing. Summary statistics are then printed out encompassing all the data that was printed out in real time up to the time when the summation option was selected. The user may also choose to print trend data over a selected period of time. The user can further select to print all the trend data over the selected period of time or only summary statistics for the selected period of time.

FIG. 10 depicts a system according to the present invention wherein probe 20 is connected to pulse oximeter 30. Upon selection of a send fax option, pulse oximeter 30 generates data in a facsimile data format which is sent via modem 40 and telephone 50 through a standard telephone jack 60 through the telecommunication switching network of local and/or long distance carriers to remote facsimile 70. Upon selection of a send to host system option, pulse oximeter 30 generates data in an ASCII data format which is sent via modem 40 and telephone 50 through a standard telephone jack 60 through the telecommunication switching network of local and/or long distance carriers to remote host system 80. Upon selection of a wait for call option, pulse oximeter 30, when called by remote host system 80, generates data in an ASCII data format which is sent via modem 40 and telephone 50 through a standard telephone jack 60 through the telecommunication switching network of local and/or long distance carriers to remote host system 80.

Figure 11:
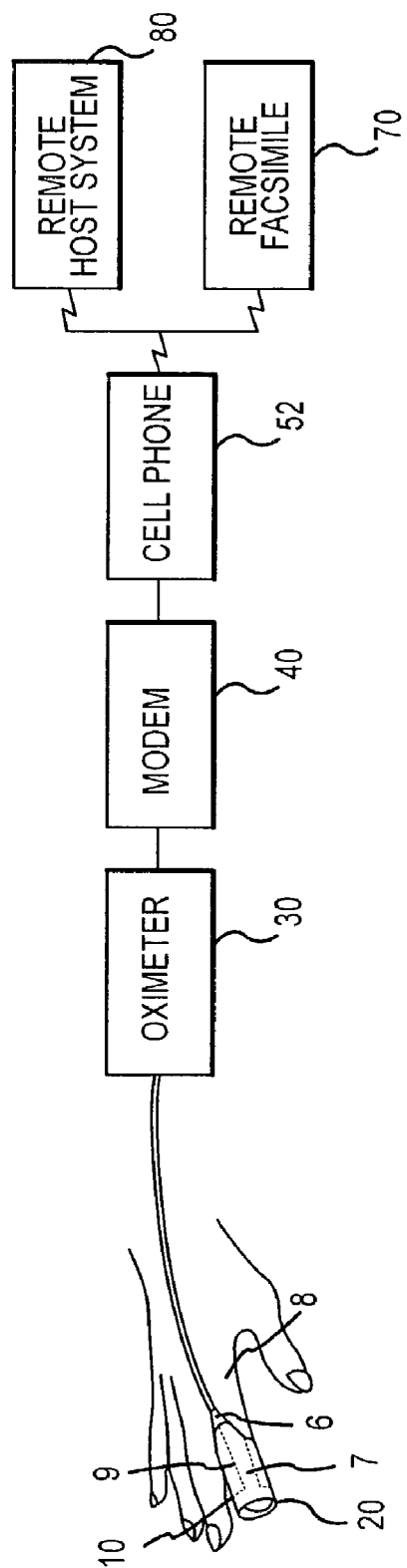
FIG. 11 is a block diagram of the embodiment of FIG. 9 further depicting alternative functional components of the system of FIG. 9.

FIG. 11 depicts an additional connection scheme where external modem 40 is compatible with cellular communication devices for transmission of the data in facsimile data format to remote facsimile 70 or ASCII data format to remote host system 80. It is also possible to use other telecommunications devices, such as digital PCS telephones or other mobile telephones or satellite telephony services. Such systems allow the pulse oximeter to be used as a portable unit with the ability to provide facsimile data format output or ASCII data format output to any remote facsimile machine independent of hard-wired connections to existing telephone systems.

Figure 12:
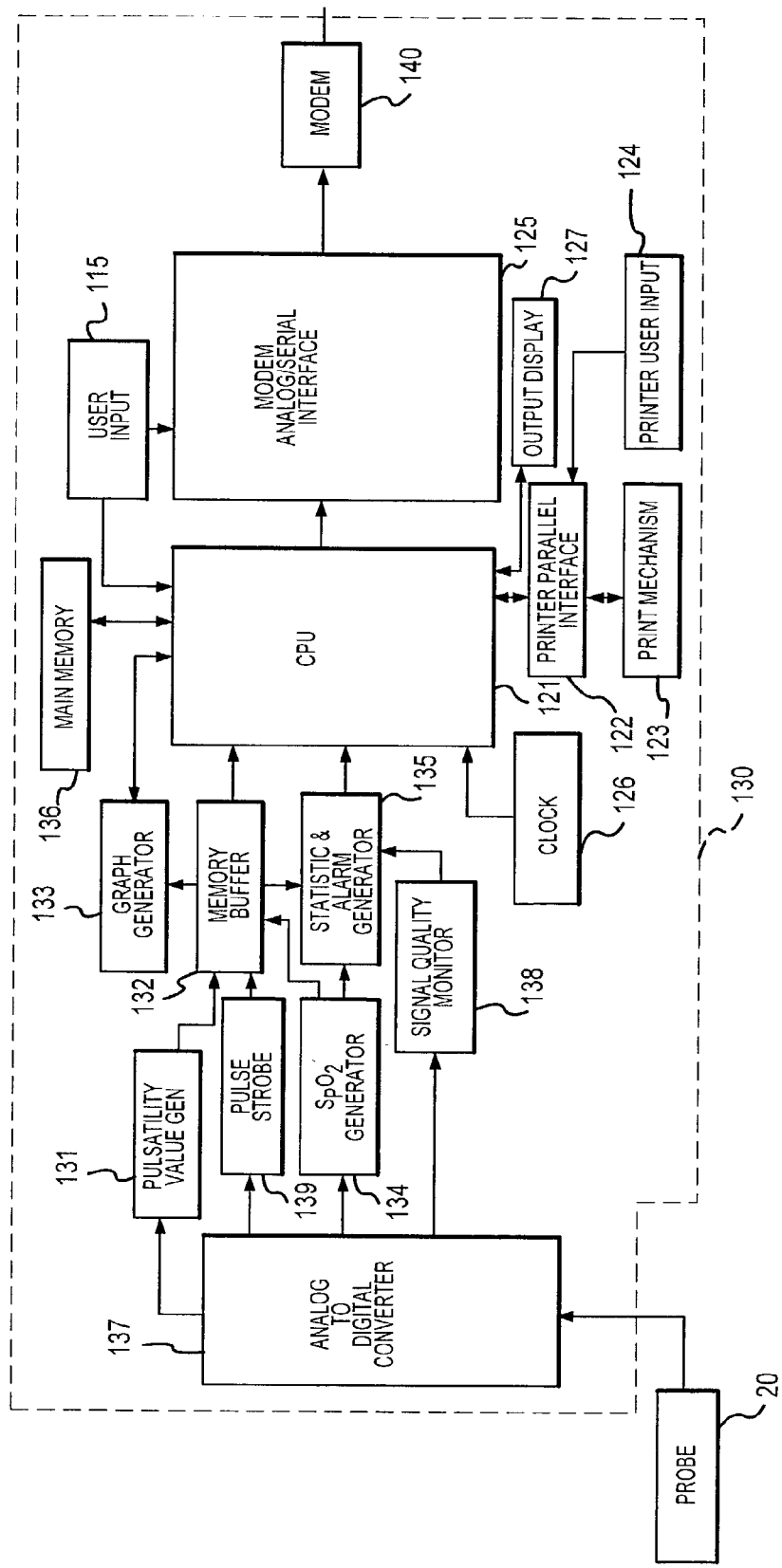
FIG. 12 is a functional block diagram of an alternative embodiment of the present invention in which the modem is internal to the photoplethysmographic device.

FIG. 12 depicts an alternate embodiment of a pulse oximeter according to the present invention. Probe 20 is connected to pulse oximeter 130 which contains essentially identical circuitry and software to the above discussed embodiment of FIG. 9 including user input 115, central processing unit 121, printer interface 122, print mechanism 123, printer user input 124, modem analog/serial interface 125, internal clock 126, output display 127, pulsatility value generator 131, memory buffer 132, graph generator 133, $SpO_2$ generator 134, statistic and alarm generator 135, main memory 136, analog-to-digital converter 137, signal quality monitor 138, and pulse strobe 139. In this alternate embodiment, however, modem 140 is internal to pulse oximeter 130, thereby reducing the number of external boxes and connections required for use of the remote facsimile function.

Figure 13:
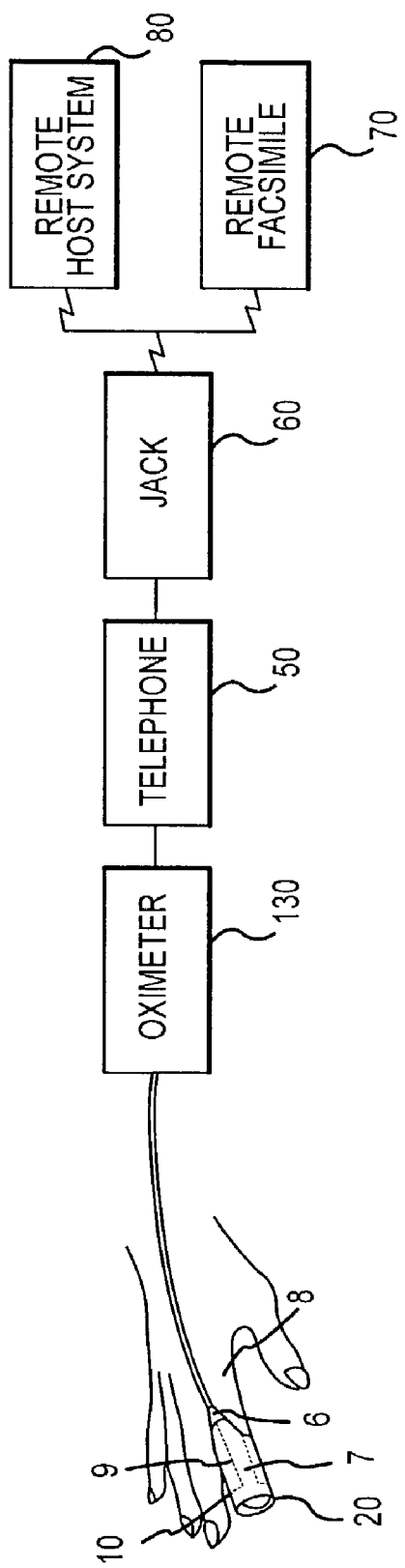
FIG. 13 is a block diagram of the alternative embodiment of FIG. 12 further depicting functional components of the system of FIG. 12.

FIG. 13 is a block diagram of the alternative embodiment of FIG. 12 further depicting functional components of the system of FIG. 12. Referring now to FIG. 13, pulse oximeter 130 with an internal modem is connected to the remote facsimile 70 or the remote host system 80 via telephone 50 and telephone jack 60.

Figure 14B:
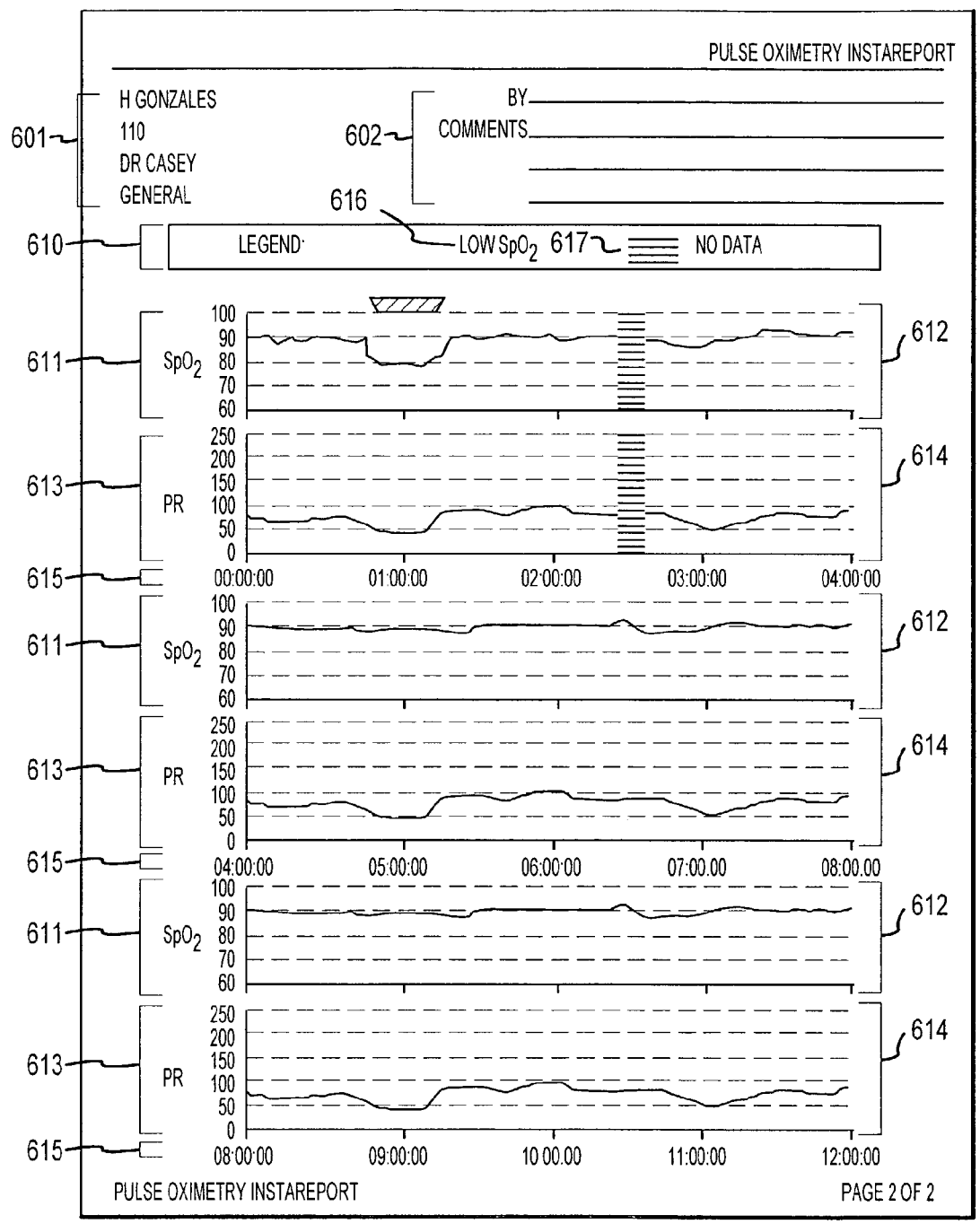

FIGS. 14A and 14B depict one embodiment of a facsimile report format for photoplethysmographic data for a device according to the present invention. Referring now to FIGS. 14A and 14B, Label Information Field 601 provides up to four lines of alphanumeric text, such as patient name, patient number, doctor name, and hospital. By And Comments Field 602 provides up to four lines of alphanumeric text, such as clinician name and any relevant comments. Data for Label Information Field 601 and By And Comments Field 602 is entered either through user input 15 which is internal to pulse oximeter 30, or through a personal computer keyboard which is in serial communication with pulse oximeter 30.

Study Start Time Field 603, Study End Time Field 604, and Study Duration Field 605 provide the date and time the data collection began, the date and time the data collection ended, and the duration of the data collection respectively. These values are derived from the internal clock 26 of pulse oximeter 30, which is also used to time-tag data.

Statistic and alarm generator 35 is responsible for generating the data found in Study Highlights Field 606, which includes the lowest $SpO_2$ value for the data printed with a corresponding Pulse Rate (PR) and time stamp. The average $SpO_2$ value, the $SpO_2$ standard deviation, the high PR rate with corresponding $SpO_2$ value and time stamp, the low PR rate with corresponding $SpO_2$ value and time stamp, and average PR are also reported. The standard deviation represents the scatter of the $SpO_2$ data points. A high standard deviation represents a wide range of $SpO_2$ values.

$SpO_2$ Values Below Field 607 shows the total number of $SpO_2$ values below the low $SpO_2$ alarm limit. Total Duration Below Field 608 shows the total amount of time for all $SpO_2$ values below the low $SpO_2$ alarm limit. The data for these fields is forwarded by the statistic and alarm generator 35 to the modem analog/serial interface 25 which then places the data in the correct fields.

Percent Time Per $SpO_2$ Range Block 609 contains a graph of the percentage of time the patient's $SpO_2$ was recorded in each of the ranges indicated. This graph is generated by graph generator 33 using data from memory buffer 32.

Alarm Legend 610 provides a legend of trend events that may occur. An event's legend symbol appears on the report at the time of occurrence. Low $SpO_2$ Symbol 616 indicates an $SpO_2$ value was recorded that was below the low alarm limit. No Data Symbol 617 indicates that no data was recorded.

$SpO_2$ Scale 611 indicates the percent scale for $SpO_2$ values displayed in the $SpO_2$ Time Graph 612. PR Range 613 indicates the beats per minute range used for PR values displayed in the PR Time Graph 614. Time Scale 615 shows the time scale used for $SpO_2$ Time Graph 612 and PR Time Graph 614. These graphs are also generated by graph generator 33 using data from memory buffer 32.

The modem analog/serial interface 25 of FIG. 9 sends the final data in the facsimile data format to remote facsimile 70 where it appears on paper in the facsimile report format of FIGS. 14A and 14B. The data format and protocol for transmissions to facsimile machines of the present invention are governed by standards established by the International Telegraph and Telephone Consultative Committee (CCITT). Telephone system standards for generating bit-images and the transmission protocol for facsimile machines may be found in publications CCITT T.4 and CCITT T.30 respectively.

Remote facsimile 70 receives a continuous stream of data from modem 40 although the facsimile data format is not generated in its entirety prior to initiation of the send data command discussed below. Rather, the data is accessed, formatted, and transmitted line by line. This enables the pulse oximeter 30 to provide a complete and detailed output to remote facsimile 70 while minimizing the use of the limited internal main memory 36 of pulse oximeter 30 until the facsimile data format is actually needed.

When remote facsimile 70 is called by pulse oximeter 30 through modem 40, one of the pieces of information exchanged in the handshaking is the speed at which remote facsimile 70 will receive data. If the data stream from pulse oximeter 30 stops, remote facsimile 70 will disconnect the telephone line. Therefore, if pulse oximeter 30 produces data line by line at a rate slower than remote facsimile 70 requires, the telephone line will be disconnected. To prevent this from happening, pulse oximeter 30 inserts and transmits zeros as filler data at the end of a first line of formatted data if the next line of formatted data is not yet ready to send. If pulse oximeter 30 generates data line by line faster than remote facsimile 70 can receive it, pulse oximeter 30 introduces delays in releasing the formatted data line by line so that remote facsimile 70 will not be overrun with data faster than it can print it.

FIG. 15 depicts one embodiment of an internal printer report format of photoplethysmographic data for a device according to the present invention. Referring now to FIG. 15, Label Information Field 701 provides up to four lines of alphanumeric text, such as patient name, patient number, doctor name, and hospital. By And Comments Field 702 provides up to four lines of alphanumeric text, such as clinician name and any relevant comments. Data for Label Information Field 701 and By And Comments Field 702 is entered either through user input 15 which is internal to the pulse oximeter 30, or through a personal computer keyboard which is in serial communication with the pulse oximeter 30.

Study Date Field 703 provides the date and time the initial data was collected. Study Start Time Field 708, Study End Time Field 709, and Study Duration Field 710 provide the date and time the data collection began, the date and time the data collection ended, and the duration of the data collection respectively. These date and time values are derived from the internal clock 26 of pulse oximeter 30, which is also used to time-tag data.

Alarm Legend 704 lists trend events that may occur and a symbol for each event. The symbols appear in Graph Field 707 at the time of occurrence. The symbols include High $SpO_2$ Symbol 716(□), Low $SpO_2$ Symbol 717(□), No Sensor Symbol 718 (!), and Sensor Off Symbol 719 (?).

Print Format Field 705 indicates the frequency at which data points are printed for this report, such as every six seconds or every thirty seconds. Header Field 706 indicates headings for the time, pulse rate, percentage scale for $SpO_2$ values, and $SpO_2$ value used for Graph Field 707 for this report. Graph Field 707 is generated by graph generator 33 using data from memory buffer 32 and contains graphical and numerical $SpO_2$ values with corresponding PR values and alarm events.

Statistic and alarm generator 35 is responsible for generating the data found in Study Highlights Field 711, which includes the lowest $SpO_2$ value for the data printed with a corresponding Pulse Rate (PR) and time stamp. The high PR rate, the low PR rate, the average $SpO_2$ value, and the $SpO_2$ standard deviation are also reported.

Percent Time Per $SpO_2$ Range Block 712 contains a graph of the percentage of time the patient's $SpO_2$ was recorded in each of the ranges indicated. Time Per $SpO_2$ Range Block 713 contains a graph of the total duration of $SpO_2$ values that occurred within each of the ranges indicated. These two graphs are generated by graph generator 33 using data from memory buffer 32.

$SpO_2$ Values Below Field 714 shows the total number of $SpO_2$ values below the low $SpO_2$ alarm limit. Total Duration Below Field 715 shows the total amount of time for all $SpO_2$ values below the low $SpO_2$ alarm limit. The data for these fields is forwarded by the statistic and alarm generator 35 to the modem analog/serial interface 25 which then places the data in the correct fields.

The printer parallel interface 22 of FIG. 9 sends the final data in the ASCII data format to printer mechanism 23 where it appears on paper in the internal printer report format of FIG. 15.

FIG. 16 depicts one embodiment of a remote computer report format of photoplethysmographic data for a device according to the present invention. Referring now to FIG. 16, Print Format Field 801 indicates the frequency at which data points are printed for this trend data report, such as every six seconds or every thirty seconds. Label Information Field 802 provides up to four lines of alphanumeric text, such as patient name, patient number, doctor name, and hospital. Data for Label Information Field 802 is entered either through the user input 15 internal to pulse oximeter 30, or through a personal computer keyboard which is in serial communication with pulse oximeter 30.

Study Date Field 803 provides the date the initial data was collected. This date value is derived from internal clock 26 of pulse oximeter 30, which is also used to time-tag data. Data Field 804 contains the capture time for numerical $SpO_2$ values, along with corresponding PR values, pulsatility values, and alarm events.

The modem analog/serial interface 25 of FIG. 9 sends the final data in the ASCII data format to remote host system 80 where when it is printed out appears on paper in the remote computer report format of FIG. 16. This report is sent when the user dials up remote host system 80 from pulse oximeter 30 and modem 40, or when a remote host system 80 calls pulse oximeter 30 through modem 40.

Figure 17:
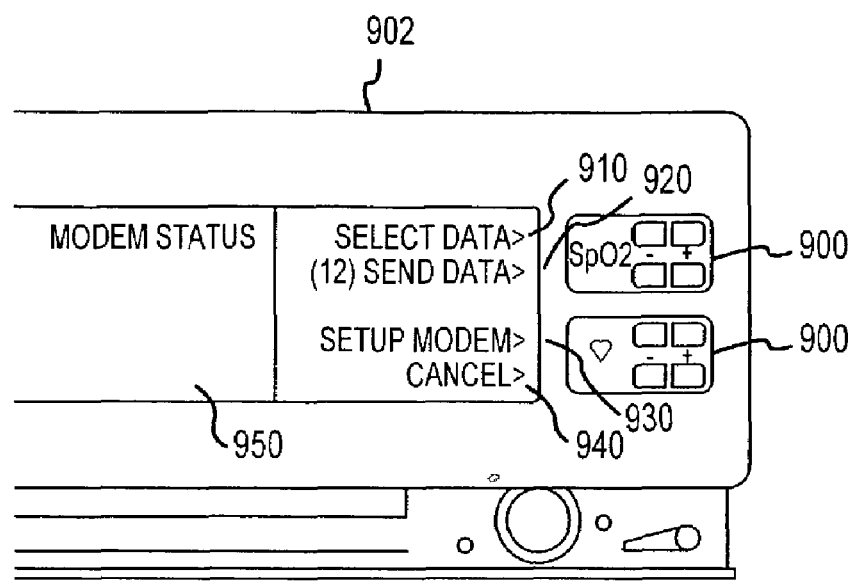
FIGS. 17 through 23 depict various user interface screens provided in an embodiment of the present invention.

FIGS. 17 through 23 depict the various user input menus according to one embodiment of the present invention. Referring now to FIG. 17, the eight function keys 900 on front panel 902 of pulse oximeter 30 are used by the user to select various functions and selections depending on the information depicted on display screen 950. In normal operation these keys are used to set alarm limits. However, in the facsimile mode the keys have different functions. A menu key (not shown in FIG. 17) located on front panel 902 et al. of pulse oximeter 30 is pressed to enter the main menu.

In the main menu four selections are displayed: MODEM, LABELS, SETTINGS, and DATE (also not shown in FIG. 17). The facsimile capability is reached by selecting MODEM.

Upon selecting the MODEM selection on the main menu of pulse oximeter 30, display screen 950 displays in FIG. 17 a modem status and four function key selections: SELECT DATA 910, SEND DATA 920, SETUP MODEM 930, and CANCEL 940. When pulse oximeter 30 is searching for modem 40, the message "SEARCHING" is displayed in display screen 950. When modem 40 is found, the message "CONNECTED" is displayed in display screen 950.

Selecting SELECT DATA 910 allows the user to select the amount of the pulse oximetry study that has been stored that the user desires to be formatted for output. The default duration is 12 hours unless there is less than 12 hours of data in memory buffer 32, and then the default is equivalent to the amount of data stored in memory buffer 32. The maximum amount of time allowed for the duration of the study is 24 hours. Selecting SELECT DATA 910 causes display screen 950 to display the content shown in FIG. 18.

Figure 18:
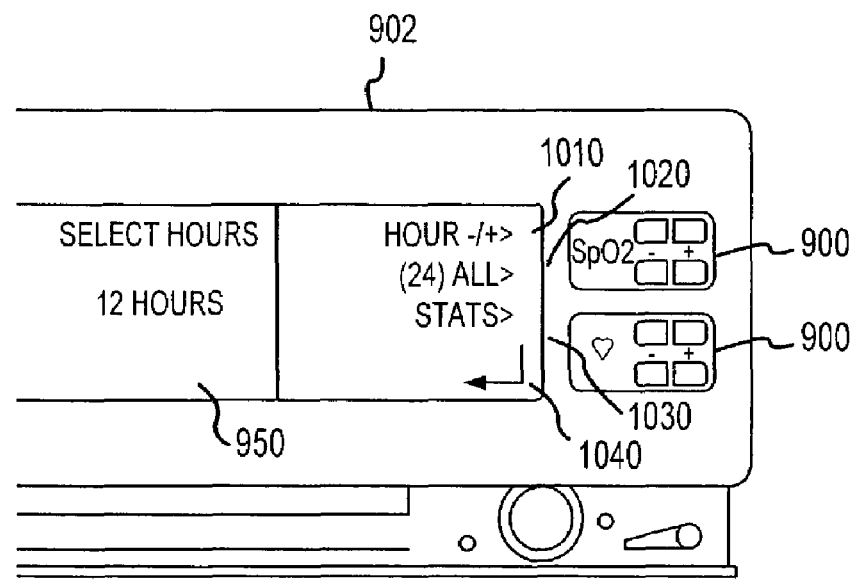

Referring now to FIG. 18, selecting HOUR−/+ 1010 enables the user to select the amount of time, in one hour increments or decrements, for which data will be formatted for output. The amount of time selected is displayed in display screen 950.

Selecting (n) ALL 1020 causes all data stored in main memory 36 to be selected. The number n in parentheses to the left of "ALL" indicates the amount of data stored in main memory 36 to the nearest hour. For example (5) ALL indicates that there are approximately five hours of data stored in main memory 36.

By selecting STATS 1030 in FIG. 18, only print headings and summary statistics for each data record within the hours selected will be output. Selecting STATS 1030 causes the word "STATS" to appear in display screen 950. Selecting return arrow 1040 returns the user to the contents of display screen 950 shown in FIG. 17.

Figure 19:
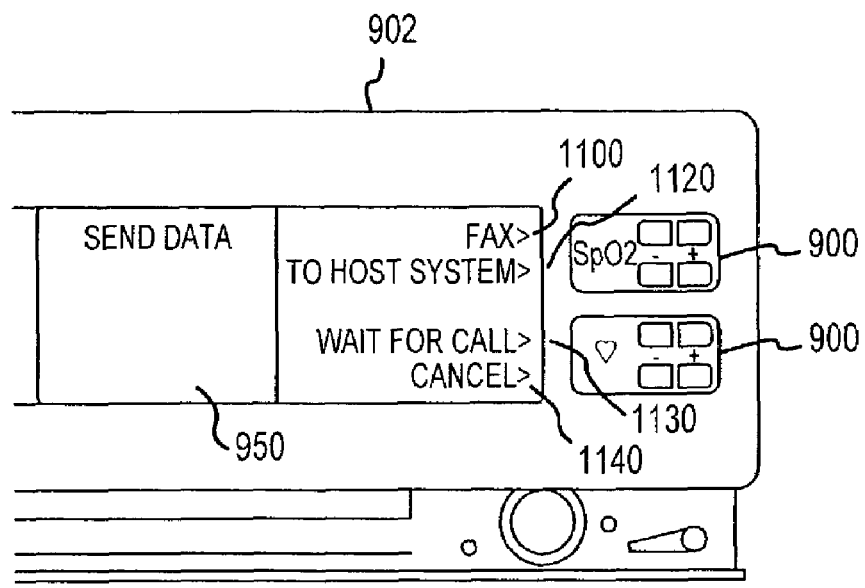

Selecting SEND DATA 920 (FIG. 17) causes display screen 950 to display the content shown in FIG. 19. Referring now to FIG. 19, the user is prompted with options regarding the sending of the selected data. These options are: FAX 1110, TO HOST SYSTEM 1120, WAIT FOR CALL 1130, and CANCEL 1140. Selecting FAX 1110 will cause the data selected to be formatted in facsimile data format for transmission, and causes display screen 950 to display the content shown in FIG. 20.

Figure 20:
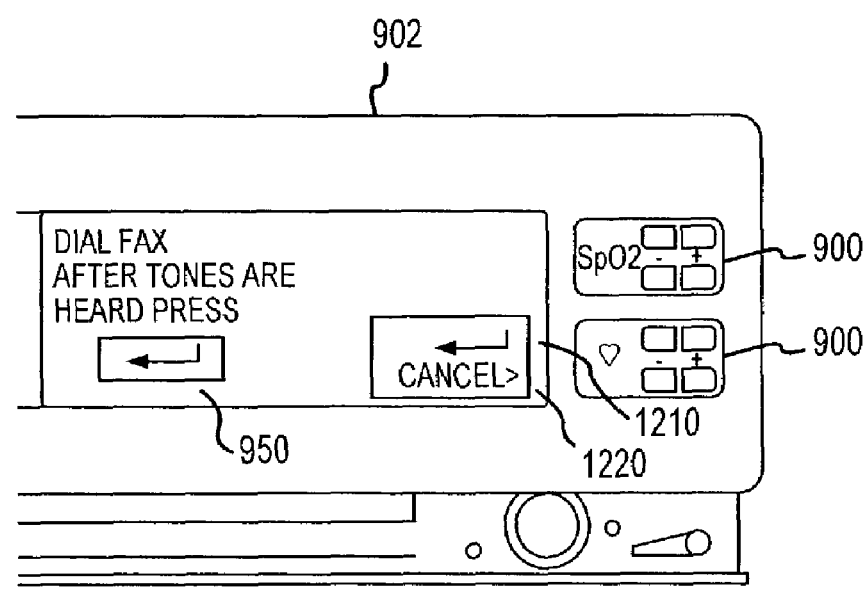

Referring now to FIG. 20, screen display 950 displays a message prompting the user to dial the remote facsimile 70 using telephone 50 and to select return arrow 1210 when the connection tone of the remote facsimile 70 is heard. In another embodiment, display screen 950 displays blanks for the user to enter the phone number for the remote facsimile 70 using user input 15 internal to pulse oximeter 30. After entering the number, selecting return arrow 1210 dials the number entered. Selecting CANCEL 1220 cancels the data sending process and returns the user to the contents of display screen 950 shown in FIG. 17.

Figure 21:
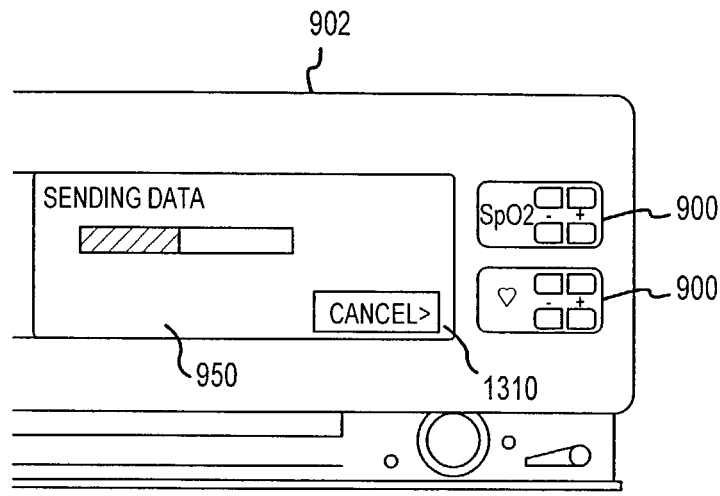

Upon selecting return arrow 1210, modem analog/serial interface 25 will begin sending the formatted data selected line by line to remote facsimile 70, and causes display screen 950 to display the content shown in FIG. 21.

Referring now to FIG. 21, DISPLAY screen 950 shows a "SENDING DATA" message and a scroll bar. The data transmission is complete when the shaded portion of the bar scrolls all the way from the left to the right. Selecting CANCEL 1310 will cause a "FAX CANCELED" message (not shown in FIG. 21) to be displayed to the user in display screen 950, and the data flow to the modem will be stopped. After a brief predetermined period of time, display screen 950 displays the content as shown in FIG. 17.

Selecting TO HOST SYSTEM 1120 (FIG. 19) will enable data to be sent to remote host system 80, which may be a central monitoring station. Selecting TO HOST SYSTEM 1120 causes display screen 950 to display the content shown in FIG. 22.

Figure 22:
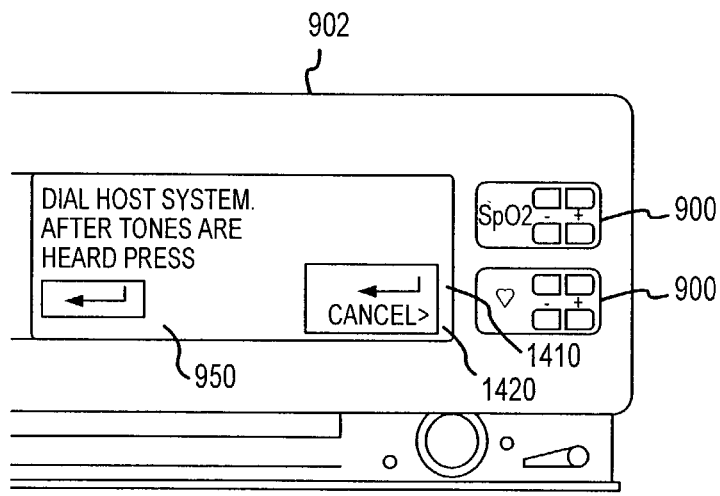

Referring now to FIG. 22, Screen display 950 prompts the user to dial remote host system 80 using telephone 50, and to select return arrow 1410 when the connection tone for remote host system 80 is heard. Data is formatted differently when TO HOST SYSTEM 1120 is selected as opposed to selecting FAX 1110. Selecting CANCEL 1420 cancels the data sending process and returns the user to the contents of display screen 950 shown in FIG. 17.

Selecting WAIT FOR CALL 1130 (FIG. 19) will enable data to be sent by pulse oximeter 30 to remote host system 80 when remote host system 80 contacts pulse oximeter 30. Selecting WAIT FOR CALL 1130 causes display screen 950 to display the content shown in FIG. 23.

Figure 23:
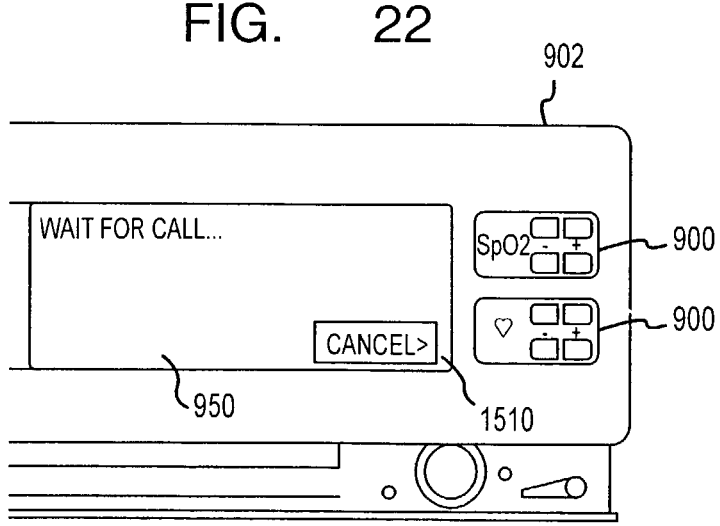

Referring now to FIG. 23, when modem 40 receives a call from remote host system 80, modem 40 arbitrates communication between remote host system 80 and pulse oximeter 30. Pulse oximeter 30 then automatically begins to transmit the selected data to remote host system 80. Screen display 950 will then display the content as shown in FIG. 21. Data is formatted differently when WAIT FOR CALL 1130 is selected as opposed to selecting FAX 1110. Selecting CANCEL 1510 cancels the data sending process and returns the user to the contents of display screen 950 shown in FIG. 17.

Information regarding the patient, doctor, and hospital can be input through user input 15, which in the preferred embodiment uses the same function keys 900 depicted in FIGS. 17 through 23. Function keys 900 are used to select alphanumeric character fields in four lines of data for the inputting of the label information. This function is well-known and has been used on the prior Model 3800 Pulse Oximeter produced by Ohmeda® Medical Systems.

Function keys 900 are also used in conjunction with SETUP MODEM 930 (FIG. 17). In this mode, the user is able to change modem settings. The preferred device is set up to use a predetermined modem, preferably a U.S. Robotics Sportster® modem. Thus, in most cases it is unnecessary for the user to change the modem settings for use of the facsimile function. If SETUP MODEM 930 is selected, the user is able to set the guard tone to either be "none", "550 Hz" of "1800 Hz" using function keys 900. Selection of a "CUSTOM" option (not shown in FIG. 17) under SETUP MODEM enables the user to set the modem initialization string to operate a modem other than the default modem described above.

Figure 24:
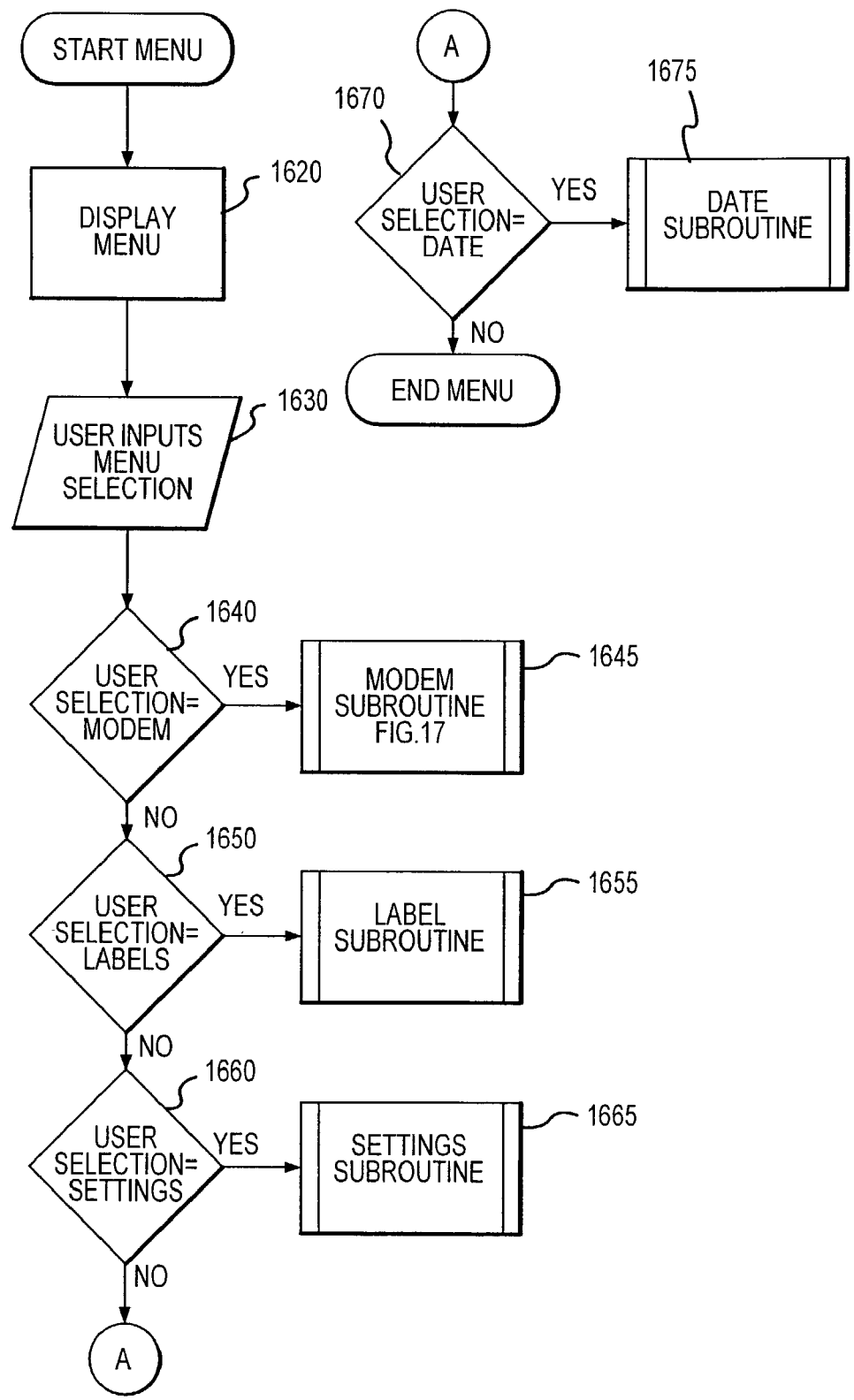
FIGS. 24 through 31 depict a series of software flow diagrams for one embodiment of the present invention.

FIGS. 24 through 31 are flow diagrams which set forth the software control necessary to implement the preferred embodiment of the present invention. Referring now to FIG. 24, the main menu is displayed in step 1620. The user inputs a menu selection in step 1630 which is then polled in steps 1640, 1650, 1660, and 1670. Control is then switched to one of the four subroutines: Modem Subroutine 1645, Label Subroutine 1655, Settings Subroutine 1665, or Date Subroutine 1675. The latter three subroutines are standard subroutines for inputting the patient, doctor, hospital data, changing oximeter settings, and setting the date. Although data stored in main memory 36 from these three subroutines is accessed by the modem analog/serial interface 25 or 110 printer parallel interface 22, they are well-known routines and are not described in detail here.

Figure 25:
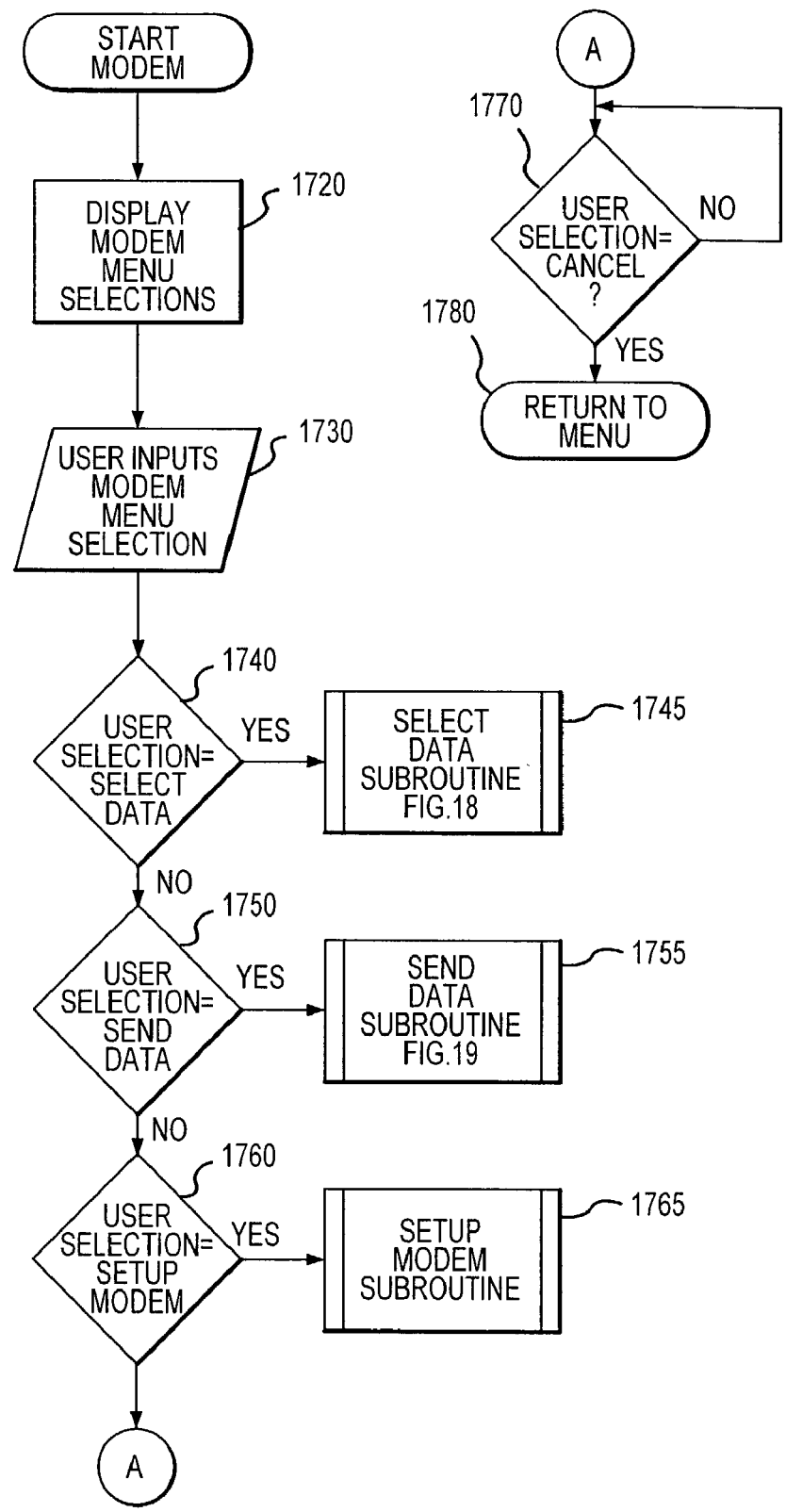

Modem Subroutine 1645 provides access to the modem analog/serial interface 25 and is depicted in greater detail in FIG. 25. Referring now to FIG. 25, upon entering the Modem Subroutine 1645 in FIG. 24, the contents of display screen 950 of FIG. 17 are displayed in step 1720. The user is thereby prompted to enter one of four menu selections in step 1730: SELECT DATA 910, SEND DATA 920, SETUP MODEM 930, OR CANCEL 940 (FIG. 17). The user input is polled in steps 1740, 1750, 1760, and 1770, and control is either switched to the appropriate subroutine or returned to the Main Menu of FIG. 24 at step 1780.

Figure 26:
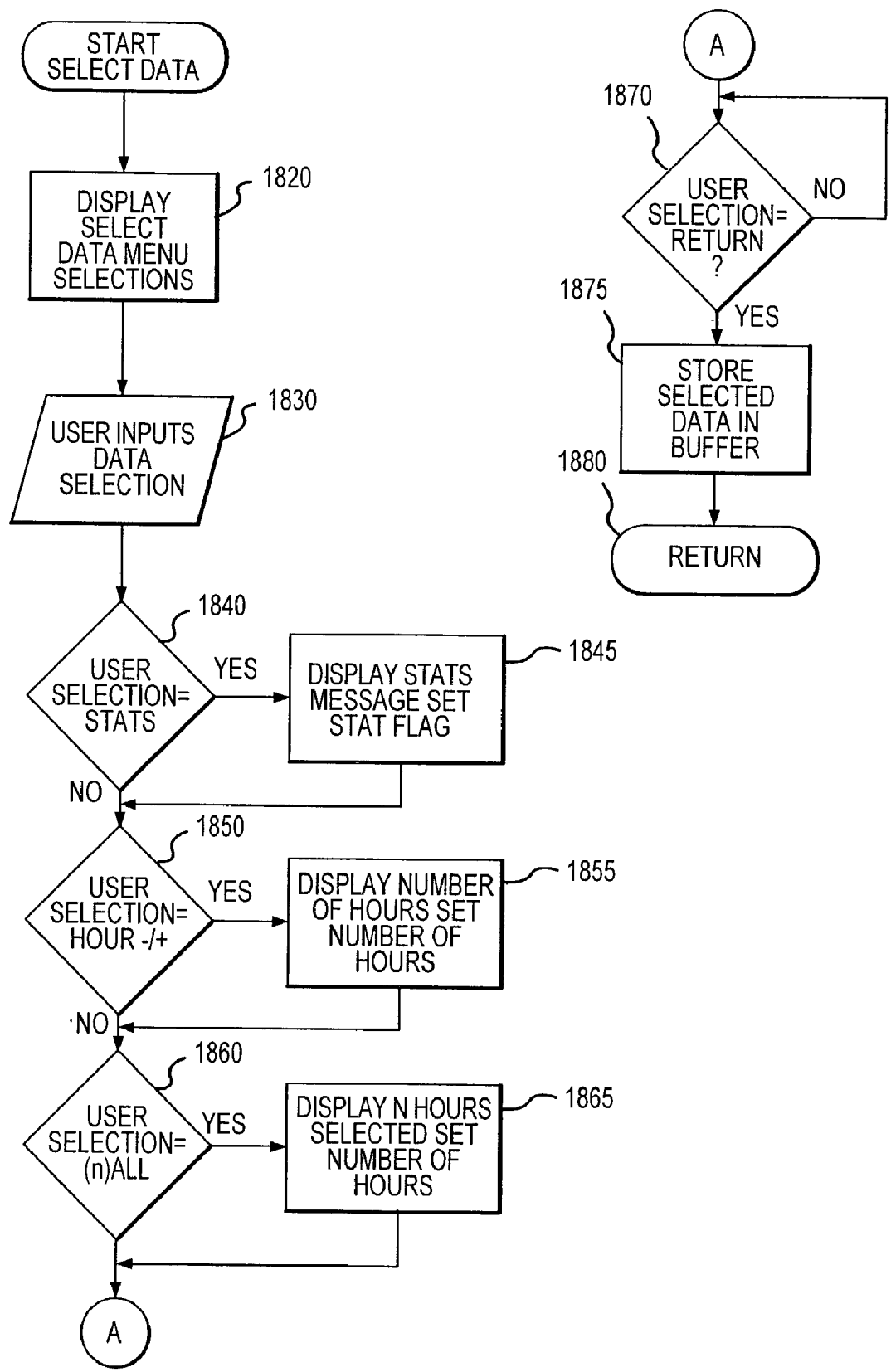

Select Data Subroutine 1745 is depicted in greater detail in FIG. 26. Referring now to FIG. 26, the contents of display screen 950 of FIG. 18 are displayed in step 1820. The user has a choice of four menu selections: HOUR–/+ 1010, (N)ALL 1020, STATS 1030, or return arrow 1040. The user inputs a selection in step 1830. The user selection is then polled in steps 1840, 1850, 1860, and 1870. Selecting STATS 1030 results in a "STATS" message being displayed to the user and a "STAT FLAG" being set at step 1845. Pulse oximeter 30 will check this flag to determine which data to select for formatting. Selecting STATS 1030 means that only a summary of the data set is provided to the user in the final output rather than all selected data.

If the user selects HOUR–/+ 1010, the number of hours displayed in display screen 950 can be incremented or decremented in one hour increments in a range from a minimum of one hour to a maximum of twenty-four hours at step 1855. If the user selects (n)ALL 1020 then all of the data available in main memory 36 is indicated for selection in step 1865. Selecting return arrow 1040 results in the selected data being stored in memory buffer 32 (FIG. 9) in step 1875, and control is returned to its calling function at step 1880.

Figure 27:
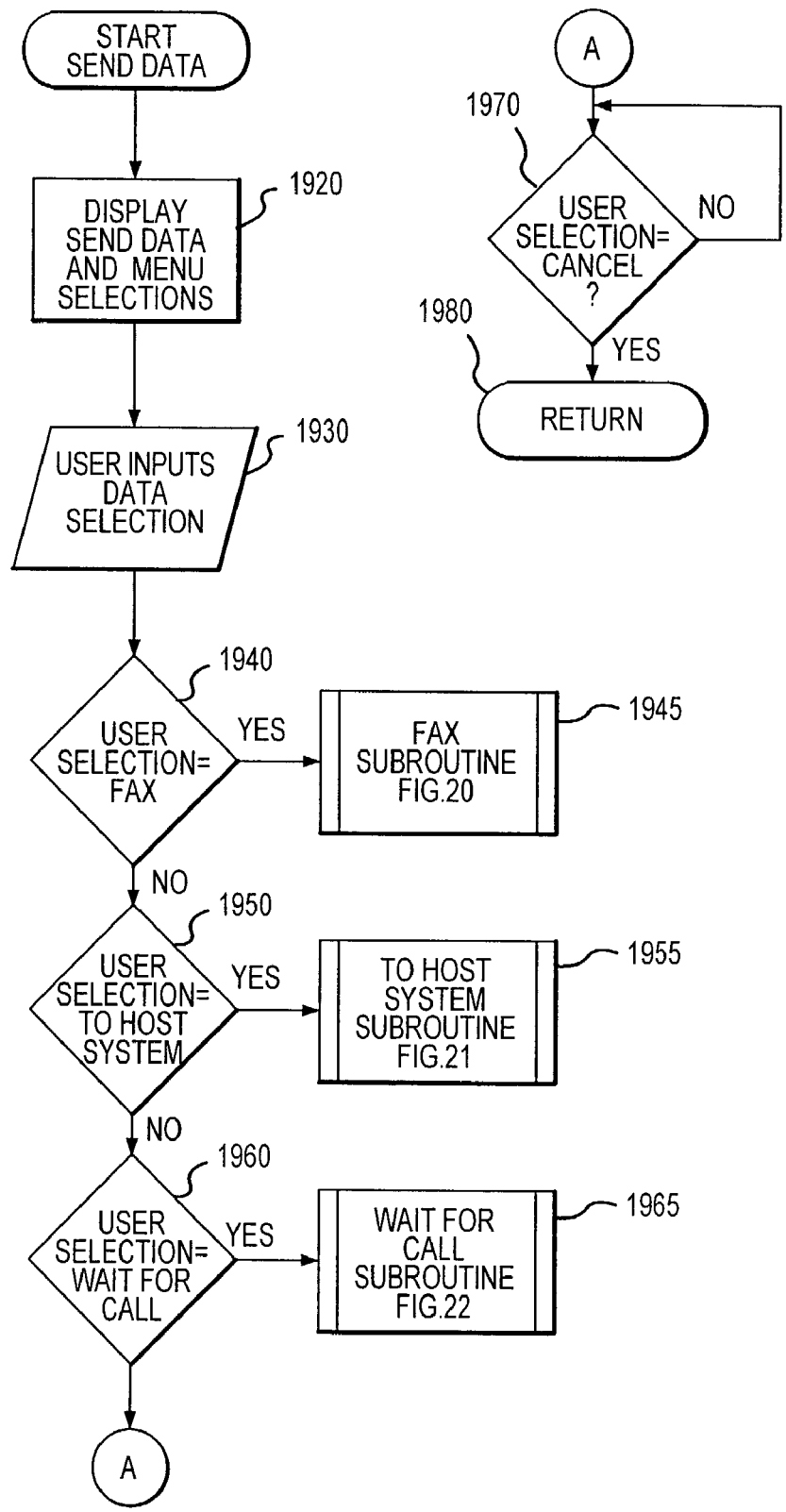

FIG. 27 depicts the flow of software control if the user selects SEND DATA 920 (FIG. 17) in step 1755 of Modem Subroutine of FIG. 25, thereby entering the Send Data Subroutine of FIG. 27. Referring now to FIG. 27, the contents of display screen 950 of FIG. 19 is displayed in step 1920. The user inputs a selection in step 1930 which is then polled in steps 1940, 1950, 1960, and 1970. Control is then-switched to one of the three subroutines, or at step 1980 control returns to step 1720 of the Modem Subroutine in FIG. 25.

Figure 28:
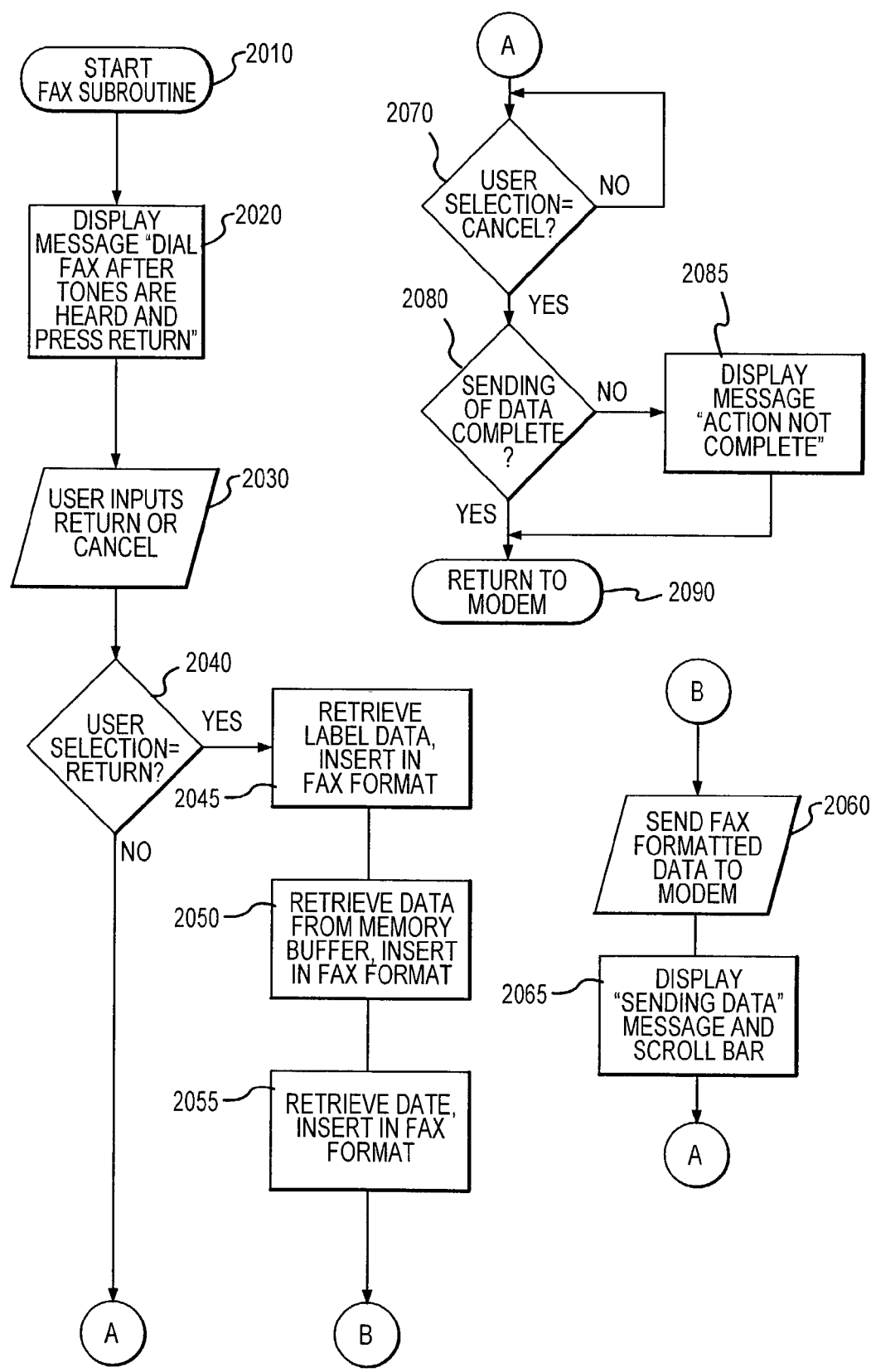

If the check in step 1940 shows that the user has selected Fax 1110 (FIG. 19) in step 1930, then control branches to Fax Subroutine 1945 and is described more fully in FIG. 28. The other two subroutines, To Host System Subroutine 1955 and wait for Call Subroutine 1965, are not part of the facsimile function, rather they are related to standard oximeter to host system connection and host initiated transfer of data. The user returns to step 1720 of the Modem Subroutine in FIG. 25 at step 1980 by selecting CANCEL 1150 (FIG. 19), which is identified in step 1970.

Referring now to FIG. 28, the contents of display screen 950 of FIG. 20 are displayed in step 1920. The message displayed prompts the user to dial the fax telephone number using telephone 50, or in another embodiment, display screen 950 displays blanks for the user to enter the phone number for the remote facsimile 70 using user input 15 internal to pulse oximeter 30. Afterwards, the user is prompted to select return arrow 1210 (FIG. 20) causing the number entered from either method to be dialed. Or, the user may choose CANCEL 1220. Thus, in step 2040 and 2070 the user input from step 2030 is polled awaiting either return arrow 1210 or CANCEL 1220. If return arrow 1210 is selected, then modem analog/serial interface 25 retrieves the information it needs from main memory 36 in order to send data in facsimile data format line by line as described above in the description of FIGS. 14A and 14B. The data is output according to the facsimile report format shown in FIGS. 14A and 14B.

In step 2045 modem analog/serial interface 25 retrieves the label data and inserts it into the facsimile data format line by line. In step 2050, modem analog/serial interface 25 retrieves the data which was previously selected by the user through the Data Selection Subroutine of FIG. 26. This data is then inserted into the facsimile data format line by line. The study date is then retrieved and inserted in the facsimile data format in step 2055. The data in facsimile data format is then-sent line by line to the modem 40 and on to the remote facsimile 70 in Step 2060. The contents of display screen 950 of FIG. 21 are displayed in step 2065, which includes a "SENDING DATA" message along with a scroll bar showing the relative amount of time to completion of the transmission. If CANCEL 1310 was selected in step 2070, then in step 2080 a second query determines if the sending of data was completed. If transmission was not complete, then an "ACTION NOT COMPLETE" message is displayed in display screen 950 at step 2085. In step 2090 control is returned to step 1720 of the Modem Subroutine of FIG. 25.

Figure 29:
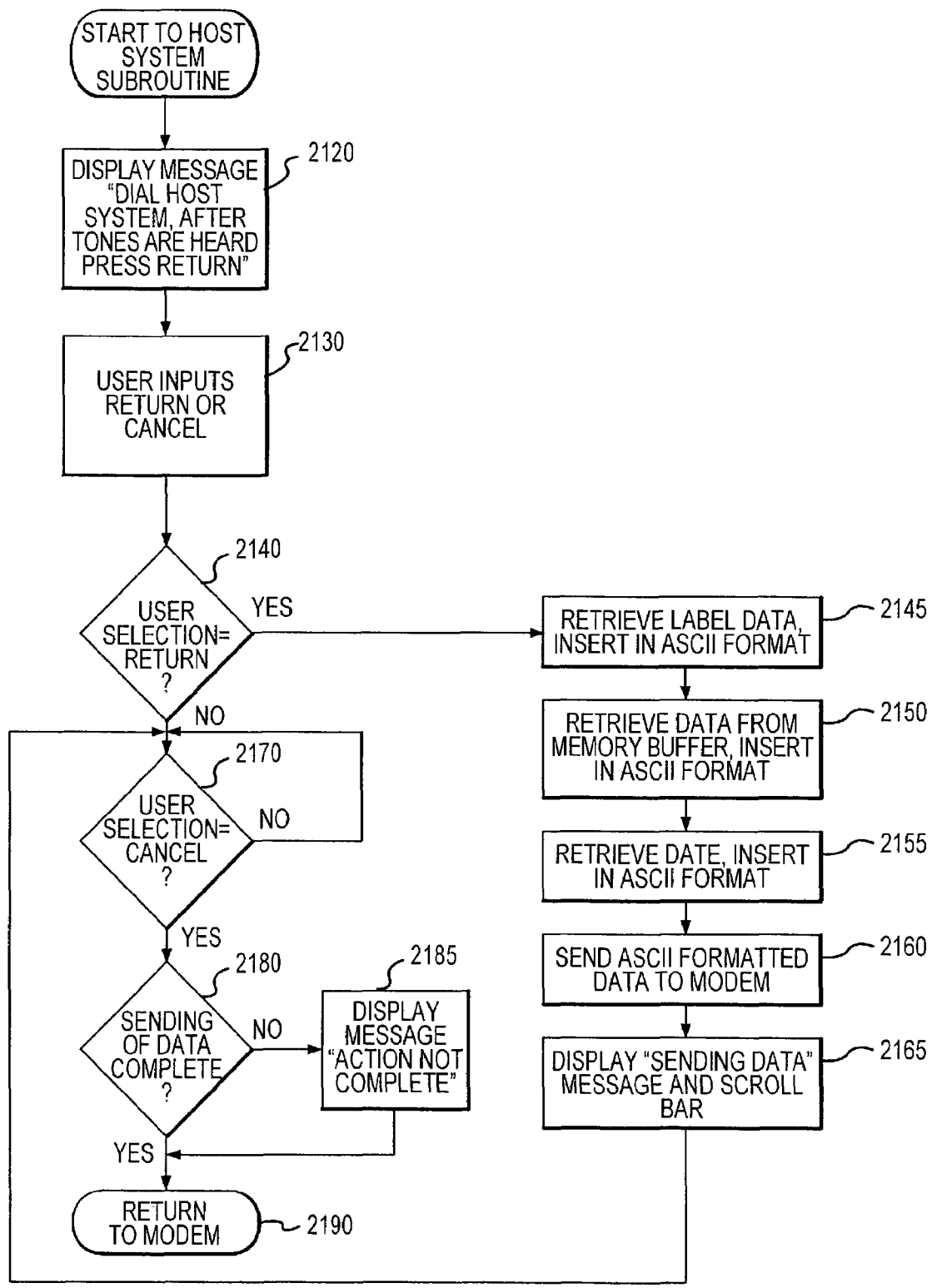

If the user has selected TO HOST SYSTEM 1120 (FIG. 19) in step 1950, then control branches to To Host System Subroutine 1955 and is described more fully in FIG. 29. Referring now to FIG. 29, the contents of display screen 950 of FIG. 22 are displayed in step 2120. The message displayed prompts the user to dial the telephone number of remote host system 80 using telephone 50. The user is also prompted to select return arrow 1410 (FIG. 22) after doing so. Or, the user may choose CANCEL 1420. Thus, in step 2140 and 2170 the user input from step 2130 is polled awaiting either return arrow 1410 or CANCEL 1420. If return arrow 1410 is selected, then modem analog/serial interface 25 retrieves the information it needs from main memory 36 in order to send data in ASCII data format. The data is output according to the remote computer report format shown in FIG. 16.

In step 2145 modem analog/serial interface 25 retrieves the label data and inserts it into the ASCII data format. In step 2150, modem analog/serial interface 25 retrieves the data which was previously selected by the user through the Data Selection Subroutine of FIG. 26. This data is then inserted into the ASCII data format. The study date is then retrieved and inserted in the ASCII data format in step 2155. The data in ASCII data format is then sent to the modem 40 and on to the remote facsimile 70 in Step 2160. The contents of display screen 950 of FIG. 21 are displayed in step 2165, which includes a "SENDING DATA" message along with a scroll bar showing the relative amount of time to completion of the transmission. If CANCEL 1420 was selected in step 2170, then in step 2180 a second query determines if the sending of data was completed. If transmission was not complete, then an "ACTION NOT COMPLETE" message is displayed in display screen 950 at step 2185. In step 2190 control is returned to step 1720 of the Modem Subroutine of FIG. 25.

Figure 30:
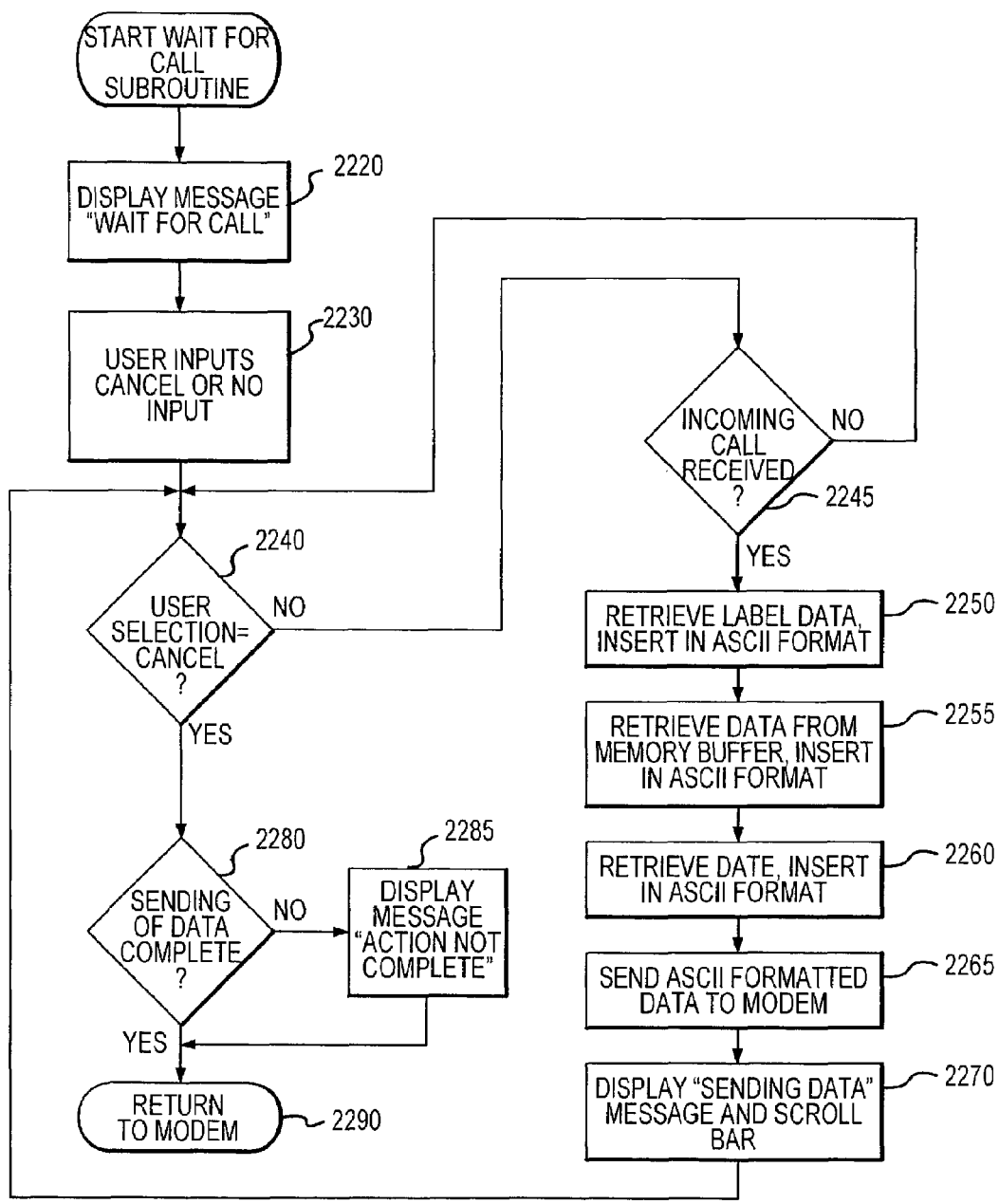

If the user has selected WAIT FOR CALL 1130 (FIG. 19) in step 1960, then control branches to Wait For Call Subroutine 1965 and is described more fully in FIG. 30. Referring now to FIG. 30, the contents of display screen 950 of FIG. 23 are displayed in step 2220. The message displayed indicates that pulse oximeter 30 is in the auto-answer mode and will send the selected data when called by remote host system 80. The user is also prompted to choose CANCEL 1510 at any time in step 2230. Thus, in step 2240 the user input, if any, from step 2230 is polled awaiting CANCEL 1510. If no user input is received, then step 2245 determines if an incoming call from remote host system 80 is received. If no call has been received, control returns to step 2240. If step 2245 determines that remote host system 80 has called, then modem analog/serial interface 25 retrieves the information it needs from main memory 36 in order to send data in ASCII data format as described above in the discussion of FIG. 16. The data is output according to the remote computer report format shown in FIG. 16.

In step 2250 modem analog/serial interface 25 retrieves the label data and inserts it into the ASCII data format. In step 2255, modem analog/serial interface 25 retrieves the data which was previously selected by the user through the Data Selection Subroutine of FIG. 26. This data is then inserted into the ASCII data format. The date is then retrieved and inserted in the ASCII data format in step 2260. The data in ASCII data format is then sent to the modem 40 and on to remote host system 80 in Step 2265. The contents of display screen 950 of FIG. 21 are displayed in step 2270, which includes a "SENDING DATA" message along with a scroll bar showing the relative amount of time to completion of the transmission. If CANCEL 1510 was selected in step 2240, then in step 2280 a second query determines if the sending of data was completed. If transmission was not complete, then an "ACTION NOT COMPLETE" message is displayed in display screen 950 at step 2285. In step 2290 control is returned to step 1720 of the Modem Subroutine of FIG. 25.

Figure 31:
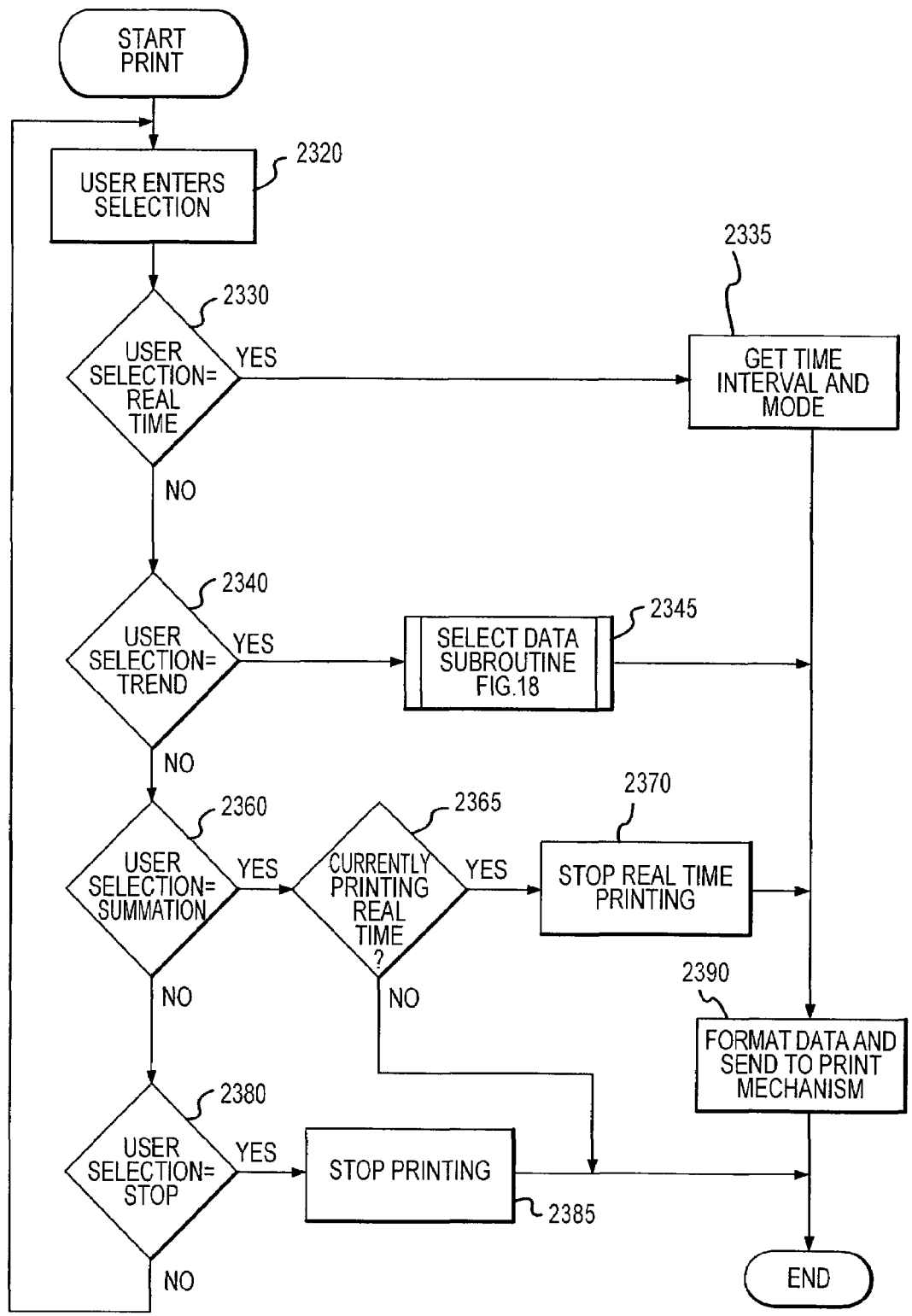

Referring now to FIG. 31, in step 2320 the user may select one of several options using printer user input 24. Thus, in steps 2330, 2340, 2360, and 2280 the user input, if any, from step 2320 is polled. If the check in step 2330 shows that the user has selected real time printing in step 2320, then step 2335 determines the current resolution selection (six second or thirty second) and the current mode setting ($SpO_2$ or PI™). Step 2390 formats the data in ASCII data format according to the determinations in step 2335, and the data in ASCII data format is sent on to print mechanism 23.

If the check in step 2340 shows that the user has selected trend printing in step 2320 then in step 2345 control is switched to the Select Data Subroutine of FIG. 26. After returning from FIG. 26, step 2390 formats in ASCII data format the trend data for the time period established by the Select Data Subroutine, and the data in ASCII data format is sent on to print mechanism 23.

If the check in step 2360 shows that the user has selected summation printing in step 2320, then step 2365 determines if print mechanism 23 is currently printing real time data. If yes, then step 2370 stops the real time printing. Step 2390 then formats in ASCII data format summary statistics for the data that was printed up to the time when the user selected the summation printing option, and the ASCII data format summary statistical data is sent on to print mechanism 23. If step 2365 determines that print mechanism is not currently printing real time data, then the user input in step 2320 is ignored and the print routine ends.

If the check in step 2380 shows that the user has selected stop printing in step 2320, then step 2385 stops any current real time printing or trend printing, and the print routine ends. If the check in step 2380 determines that the user has not selected stop printing, then no user input was entered in step 2320, and control returns step 2320 to await user input.

Thus the apparatus of the present systems enables a user to select a set of photoplethysmographic data for formatting in facsimile data format and transmitting to a remote facsimile machine, formatting in ASCII data format and transmitting to a remote host system, formatting in ASCII data format and transmitting when called by a remote host system, and also formatting in ASCII data format and printing to an internal printer.

While the apparatus disclosed herein illustrates the concepts of the invention, there is no intention to limit the scope of the invention to this specific apparatus. It is expected that those skilled in the art can devise alternate implementations of the display system, which alternate implementations are intended to fall within the scope of the appended claims.

What is claimed is:

1. An apparatus for outputting patient data for receipt by a remote host, comprising:
   a photoplethysmographic sensor which monitors a patient and generates analog data corresponding to a plurality of illumination signals detected by said sensor;
   an analog-to-digital converter which converts at least a portion of said analog data received from said sensor;
   a memory for storing digital data received from said analog-to-digital converter;
   a blood oxygen content generator for generating at least a first set of medical parameters related at least in part to blood oxygen saturation values from said digital data received from said analog-to-digital converter;
   a processor in communication with said memory and said blood oxygen generator being operative to format said set of medical parameters into formatted data for transfer to a remote host, wherein said formatted data defines, in addition to said set of medical parameters, at least one display layout of said set of medical parameters for at least a first output at said remote host;
   a network interface for transmission of said formatted data across a communication network to said remote host.

2. The apparatus of claim 1, wherein said processor formats said set of medical parameters into an ASCII data format type for transfer to said remote host.

3. The apparatus of claim 1, wherein said network interface provides access to a telephony communications network for transmission of said formatted data.

4. The apparatus of claim 3, wherein said network interface further includes:
   a digital-to-analog converter for converting said formatted data into an analog signal for transmission to a remote host via said telephony communications network, wherein said set of medical parameters in said formatted data are output according to said display layout of said formatted data.

5. The apparatus of claim 4, wherein said formatted data defines a display layout for a printed output at said remote host.

6. The apparatus of claim 5, wherein said formatted data defines a display layout for use with a facsimile machine.

7. The apparatus of claim 1, wherein said set of medical parameters includes at least one of: a blood oxygen concentration, a perfusion index, a pulse rate, blood carbon dioxide concentration, and methemoglobin concentration.

8. The apparatus of claim 1, wherein said formatted data further includes at least one of a patient's name, hospital name, doctor's name, date, time of test, lowest blood analyte level, highest blood analyte level, lowest pulse rate, highest pulse rate, high pulse rate duration, low pulse rate duration, recording duration, low blood analyte level duration, sensor off alarm, no sensor alarm, pulsatility value, blood analyte concentration value, blood analyte concentration by range, blood analyte concentration histogram, blood analyte concentration event chart, and average blood analyte concentration.

9. The apparatus of claim 1, further comprising:
a user input operatively associated with said processor for inputting selections regarding said set of medical parameters to be formatted.

10. The apparatus of claim 1, wherein said at least one display layout defined for said set of medical parameters includes layout information for at least one of graphical information associated with at least one parameter of said set of medical parameters and textual information associated with at least one parameter of said medical parameters.

11. The apparatus of claim 10, wherein said layout information for each said parameter includes at least one of display location, display size, display color, and display font for said at least one output.

12. An apparatus for receiving monitored patient data via a communications network, comprising:
a network interface for receiving formatted photoplethysmographic data across a communication network, wherein said formatted photoplethysmographic data contains at least a first set of medical parameters formatted with at least one set of display layout information for use in providing an output of said set of medical parameters;
a processor associated with said network interface operative to receive said formatted data and separate said medical parameters from said display layout information; and
an output device in communication with said processor, wherein said output device produces a display output of at least one of said set of medical parameters according to said display layout information.

13. The apparatus of claim 12, wherein said network interface comprises a modem selectively attachable to a telephony communications network.

14. The apparatus of claim 12, wherein said formatted data comprises data formatted according to an ASCII data format.

15. The apparatus of claim 12, wherein said output device comprises a facsimile operable to print at least one of said set of medical parameters according to said display layout information.

* * * * *